(12) United States Patent
Allen et al.

(10) Patent No.: US 7,029,655 B2
(45) Date of Patent: Apr. 18, 2006

(54) MAGNETIC RESONANCE IMAGING AGENTS FOR IN VIVO LABELING AND DETECTION OF AMYLOID DEPOSITS

(75) Inventors: Matthew J. Allen, Pasadena, CA (US); Scott Fraser, La Canada, CA (US); Russell E. Jacobs, Pasadena, CA (US); Thomas J. Meade, Alta Dena, CA (US)

(73) Assignee: California Institute of Technology, Pasadena, CA (US)

( * ) Notice: Subject to any disclaimer, the term of this patent is extended or adjusted under 35 U.S.C. 154(b) by 443 days.

(21) Appl. No.: 09/972,302

(22) Filed: Oct. 4, 2001

(65) Prior Publication Data

US 2002/0098153 A1 Jul. 25, 2002

Related U.S. Application Data

(60) Provisional application No. 60/238,231, filed on Oct. 4, 2000, and provisional application No. 60/285,379, filed on Apr. 20, 2001.

(51) Int. Cl.
*A61B 5/055* (2006.01)

(52) U.S. Cl. ............... 424/9.36; 424/9.361; 424/9.363; 424/9.364

(58) Field of Classification Search ............... 424/9.36, 424/9.361, 9.363, 9.364; 560/76, 89
See application file for complete search history.

(56) References Cited

U.S. PATENT DOCUMENTS

| | | | |
|---|---|---|---|
| 4,637,988 A | 1/1987 | Hinshaw et al. | |
| 4,647,447 A | 3/1987 | Gries et al. | |
| 4,678,667 A | 7/1987 | Meares et al. | |
| 4,822,594 A | 4/1989 | Gibby | |
| 4,837,169 A | 6/1989 | Toner | |
| 4,877,872 A | 10/1989 | Morgan et al. | |
| 4,885,363 A | 12/1989 | Tweedle et al. | |
| 5,087,440 A | 2/1992 | Cacheris et al. | |
| 5,095,099 A | 3/1992 | Parkinson et al. | |
| 5,133,956 A | 7/1992 | Garlich et al. | |
| 5,155,215 A | 10/1992 | Ranney | |
| 5,188,816 A | 2/1993 | Sherry et al. | |
| 5,219,553 A | 6/1993 | Kraft et al. | |
| 5,230,883 A | 7/1993 | Kornguth et al. | |
| 5,256,395 A | 10/1993 | Barbet et al. | |
| 5,262,532 A | 11/1993 | Tweedle et al. | |
| 5,292,414 A | 3/1994 | Sessler et al. | |
| 5,310,539 A | 5/1994 | Williams | |
| 5,322,681 A | 6/1994 | Klaveness | |
| 5,332,567 A | 7/1994 | Goldenberg | |
| 5,338,532 A | 8/1994 | Tomalia et al. | |
| 5,358,704 A | 10/1994 | Desreux et al. | |
| 5,407,657 A | 4/1995 | Unger et al. | |
| 5,419,893 A | 5/1995 | Berg et al. | |
| 5,446,145 A | 8/1995 | Love et al. | |
| 5,466,438 A | 11/1995 | Unger et al. | |
| 5,466,439 A | 11/1995 | Gibby et al. | |
| 5,531,978 A | 7/1996 | Berg et al. | |
| 5,554,748 A | 9/1996 | Sieving et al. | |
| 5,622,821 A | 4/1997 | Selvin et al. | |
| 5,707,605 A | 1/1998 | Meade et al. | |
| 5,900,228 A | * 5/1999 | Meade et al. ............ 424/9.363 |
| 5,914,095 A | 6/1999 | Watson | |
| 5,955,605 A | 9/1999 | Axworthy et al. | |
| 5,980,862 A | 11/1999 | Meade et al. | |
| 6,054,114 A | * 4/2000 | Lansbury, Jr. et al. ..... 424/1.11 |

FOREIGN PATENT DOCUMENTS

| | | |
|---|---|---|
| CA | 2197074 | 8/1994 |
| CA | 2139374 | 7/1995 |
| CA | 2182686 A1 | 8/1995 |
| WO | WO 90/12050 | 10/1990 |
| WO | WO 92/19264 | 11/1992 |
| WO | WO 95/27705 | 10/1995 |
| WO | WO 95/28966 | 11/1995 |
| WO | WO 95/31444 | 11/1995 |
| WO | WO 95/32741 | 12/1995 |
| WO | WO 96/23526 | 8/1996 |
| WO | WO 96/38184 | 12/1996 |
| WO | WO 97/21431 | 6/1997 |
| WO | WO 97/32862 | 9/1997 |
| WO | WO 97/36619 | 10/1997 |
| WO | WO 99/21592 | 5/1999 |

OTHER PUBLICATIONS

Aguayo, J.B., et al. "Nuclear Magnetic Resonance Imaging of a Single Cell," Nature, Letters to Nature 322:190–191 (Jul. 10, 1986).
Alexander, "Design and Synthesis of Macrocyclic Ligands and Their Complexes of Lanthanides and Antinides," Chem. Review, 95:273–342 (1995).
Borch, R.F., et al. "The Cyanohydridoborate Anion as a Selective Reducing Agent," Journal of the American Chemical Society 93(12):2897–2904 (Jun. 16, 1971).
Cho, Z.H., et al. "Some Experiences on a 4μμm NMR Microscopy," Book of Abstracts, vol. 1, p. 233, Society of Magnetic Resonance in Medicine, 6th Annual Meeting and Exhibition, Aug. 17–21, 1987, New York City, NY.
Grynkiewicz, G., et al. "A New Generation of Ca2+ Indicators with Greatly Improved Fluorescence Properties," The Journal of Biological Chemistry, 260(6):3440–3450 (1985).
Hennessy, M.J., et al. "NMR Surface Coil Microscopy," Book of Abstracts, vol. 2, p. 461–462, Society of Magnetic Resonance in Medicine, 5th Annual Meeting and Exhibition, Aug. 19–22, 1986, Montreal, Quebec, Canada.
Hoult, D.I., et al. "The Signal–to–Noise Ratio of the Nuclear Magnetic Resonance Experiment," Journal of Magnetic Resonance, 24: 71–85 (1976).

(Continued)

*Primary Examiner*—Michael G. Hartley
(74) *Attorney, Agent, or Firm*—Robin M. Silva, Esq.; Renee M. Kosslak, Esq.; Dorsey & Whitney LLP

(57) ABSTRACT

The invention relates to a novel class of magnetic resonance imaging agents that can cross the blood brain barrier and provide accurate magnetic resonance imaging of the brain, especially magnetic resonance images of amyloid deposits associated with Alzheimer's disease.

15 Claims, 15 Drawing Sheets

OTHER PUBLICATIONS

Jackels, "Section III: Enhancement Agents for Magnetic Resonance and Ultrasound Imaging. Chapter 20: Enhancement Agents for Magnetic Resonance Imaging: Fundamentals," Pharm. Med. Imag. Section III, Chap. 20, pp. 645–661 (1990).

Jacobs and Fraser, "Magnetic Resonance Microscopy of Embryonic Cell Lineages and Movements," *Science*, 263:681–684 (1994).

Johnson, G.A., et al., "MR Microscopy at 7.0 T," Works in Progress, Society of Magnetic Resonance in Medicine, Sixth Annual Meeting and Exhibition, Aug. 17–21, 1987, New York City, NY. p. 23.

Li, et al., "A Calcium–Sensitive Magnetic Resonance Imaging Contrast Agent," J. Am. Chem. Soc., 121:1413–1414 (1999).

Meade, T.J. et al., "Hydrophobic, Regiospecific Guest Binding by Transition–Metal Host Complexes Having Permanent Voids as Revealed by FT–NMR Relaxation Studies," J. Am. Chem. Soc., 108:1954–1962 (1986).

Meyer et al., "Advances in Macrocyclic Gadolinium Complexes as Magnetic Resonance Imaging Contrast Agents," Investigative Radiology, 25(1):S53–S55 (Sep. 1990).

Moats, et al., "A "Smart" Magnetic Resonance Imaging Agent That Reports on Specific Enzymatic Activity," Angew. Chem. Int. Ed. Engl., 36(7):726–728 (Apr. 1997).

Moi, M.K., et al. "The Peptide Way to Macrocyclic Bifunctional Chelating Agents: Synthesis of 2– (p–Nitrobenzyl) –1,4,7,10–tetraazacyclododecan– N, N, N, N–tetraacetic Acid and Study of Its Yttrium (III) Complex," J. Am. Chem. Soc. 110(18):6266–6267 (1988).

Nijhof, E.J., et al. "High–Resolution Proton Imaging at 4.7 Tesla," Proceedings of Soc. Magn. Reson. Med., p. 925 (1987).

Runge, V.M., et al. "Future Directions in Magnetic Resonance Contrast Media," Top Magn. Reson. Imaging., 3(2):85–97 (1991).

Russell, E.J., et al. "Multicenter Double–Blind Placebo––Controlled Study of Gadopentetate Dimeglumine as an MR Contrast Agent: Evaluation in Patients with Cerebral Lesions," American Journal of Roentgenology, 152:813–823 (Apr. 1989).

Shukla, et al., "Design of Conformationally Rigid Dimeric MRI Agents," Magnetic Resoance in Medicine, 36(6): 928–931 (1996).

Sillerud, L.O., et al. "Proton NMR Microscopy of Intact Multicellular Tumor Spheroids," Book of Abstracts, vol. 1, p. 468, Society of Magnetic Resonance in Medicine, 6th Annual Meeting and Exhibition, Aug. 17–21, 1987, New York City, NY.

Staubli and Meade, "The Design and Synthesis of Fluorescently Detectable Magnetic Resonance imaging Agents for Embryonic Cell Lineage Analysis," *American Chemical Society: Division of Inorganic Chemistry*, 209th ACS National Meeting, Anaheim, California. Abstract No. 385 (Apr. 2–6, 1995).

Tsien, R.Y. "New Calcium Indicators and Buffers with High Selectivity Against Magnesium and Protons: Design, Synthesis, and Properties of Prototype Structures," Biochemistry, 19(11):2396–2404 (1980).

Tweedle, M.F., et al. "Considerations Involving Paramagnetic Coordination Compounds as Useful NMR Contrast Agents," Nucl. Med. Bio. 15(1):31–36 (1988).

* cited by examiner

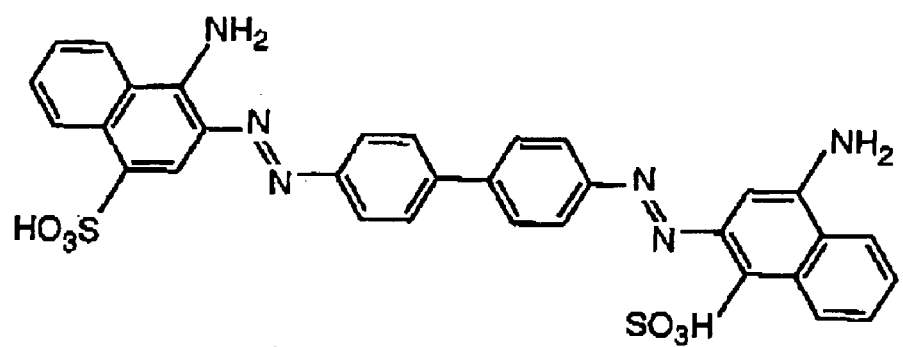
FIG._1A
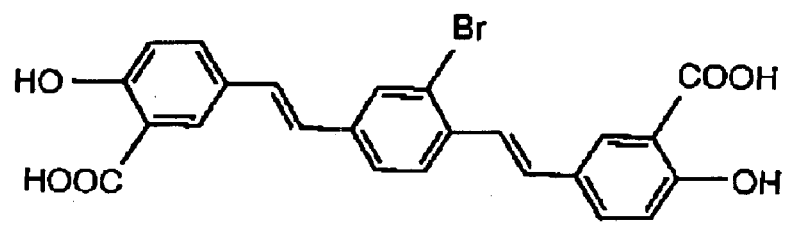
FIG._1B
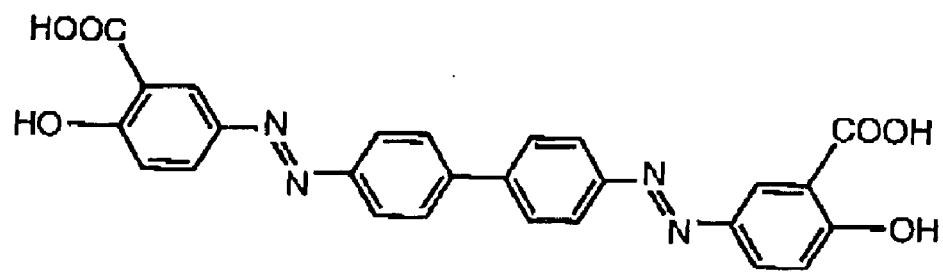
FIG._1C

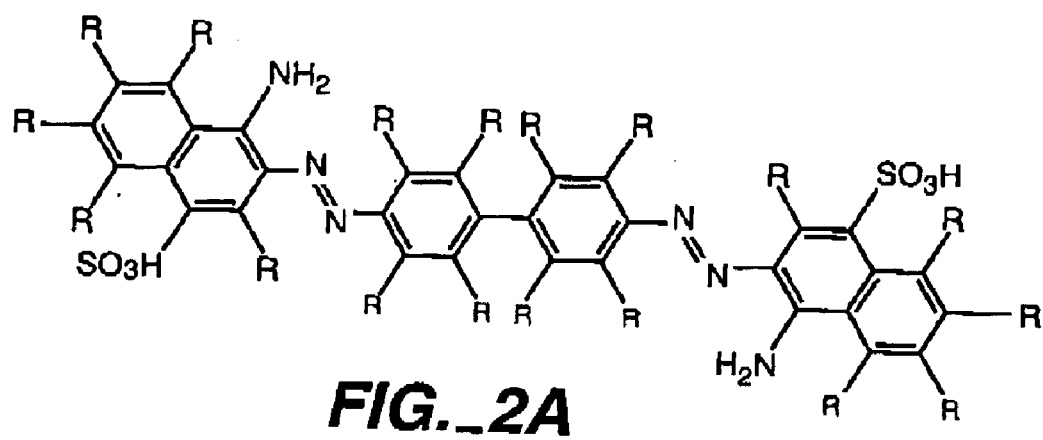
FIG._2A
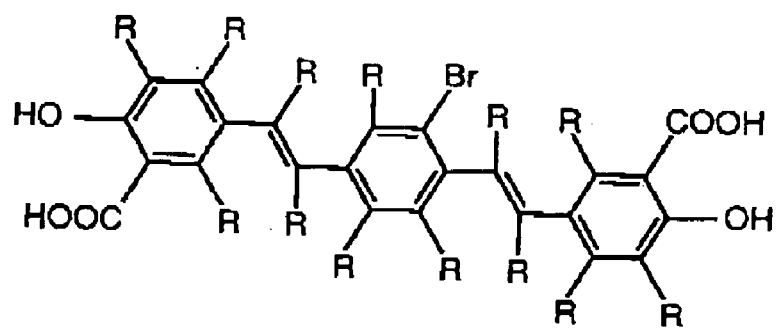
FIG._2B
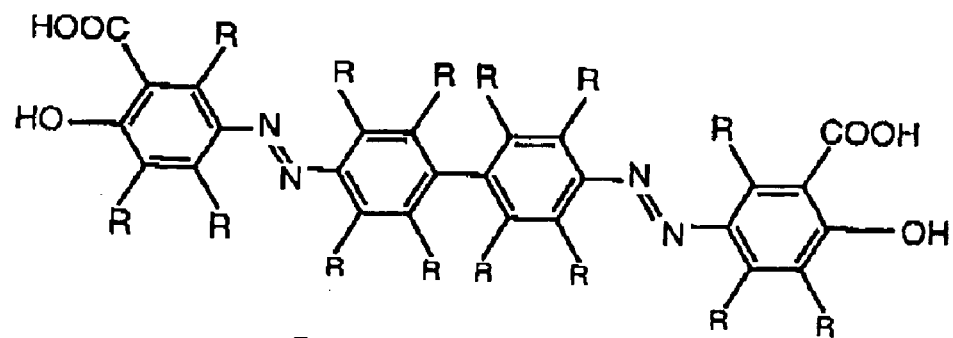
FIG._2C

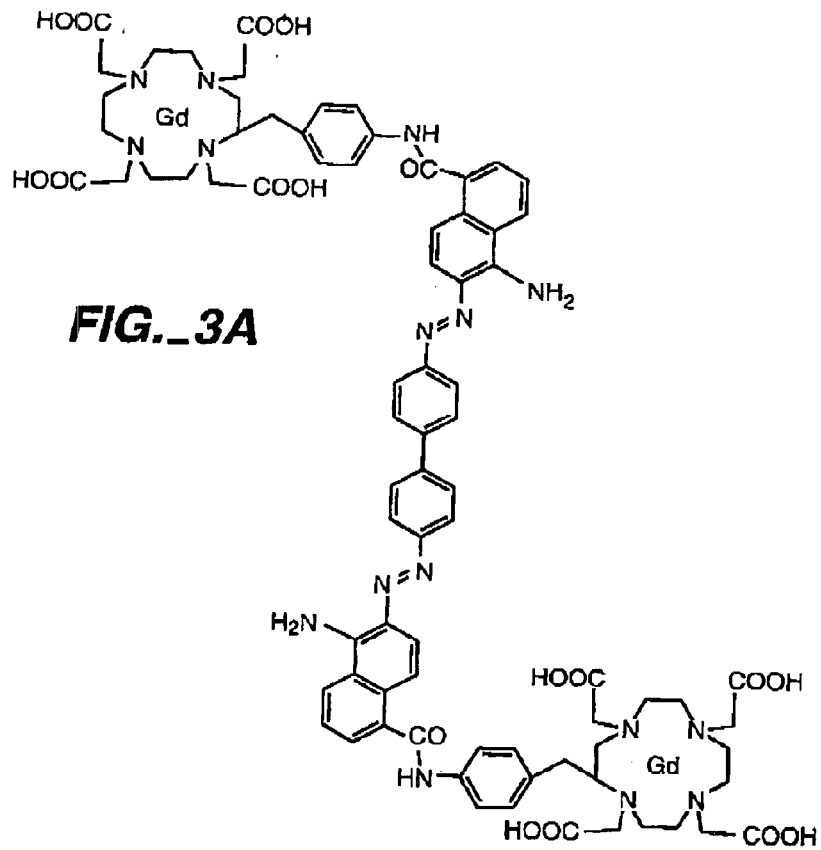
*FIG._3A*
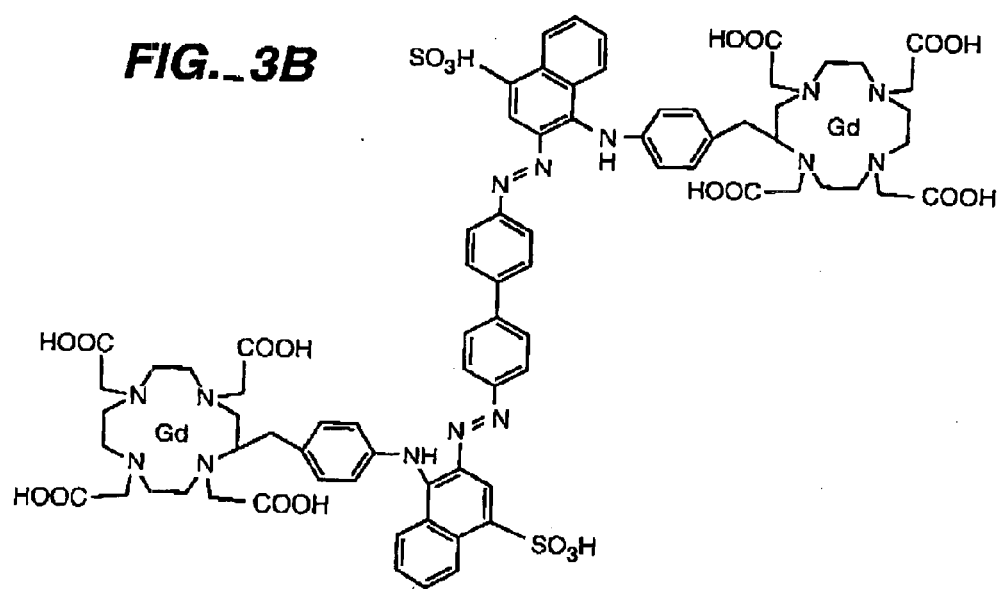
*FIG._3B*

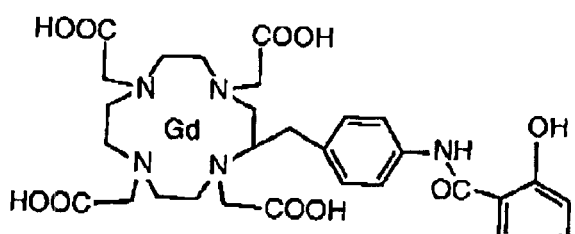
FIG._3C
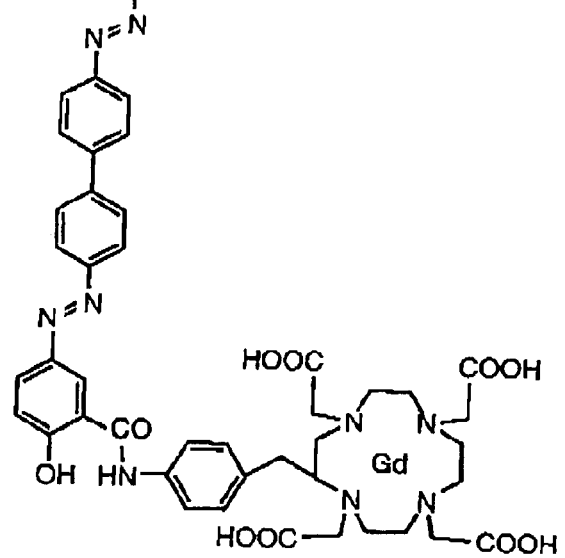
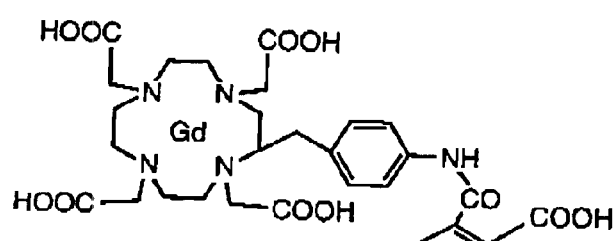
FIG._3D
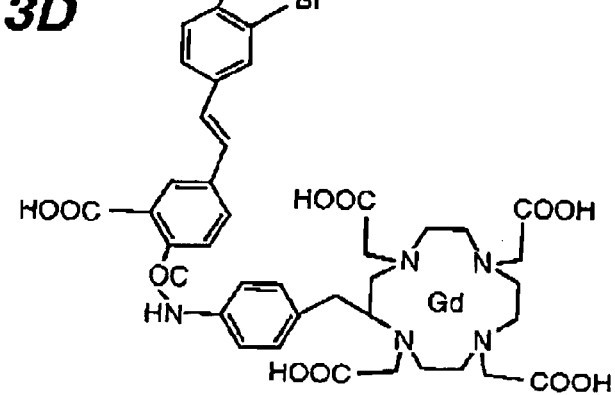

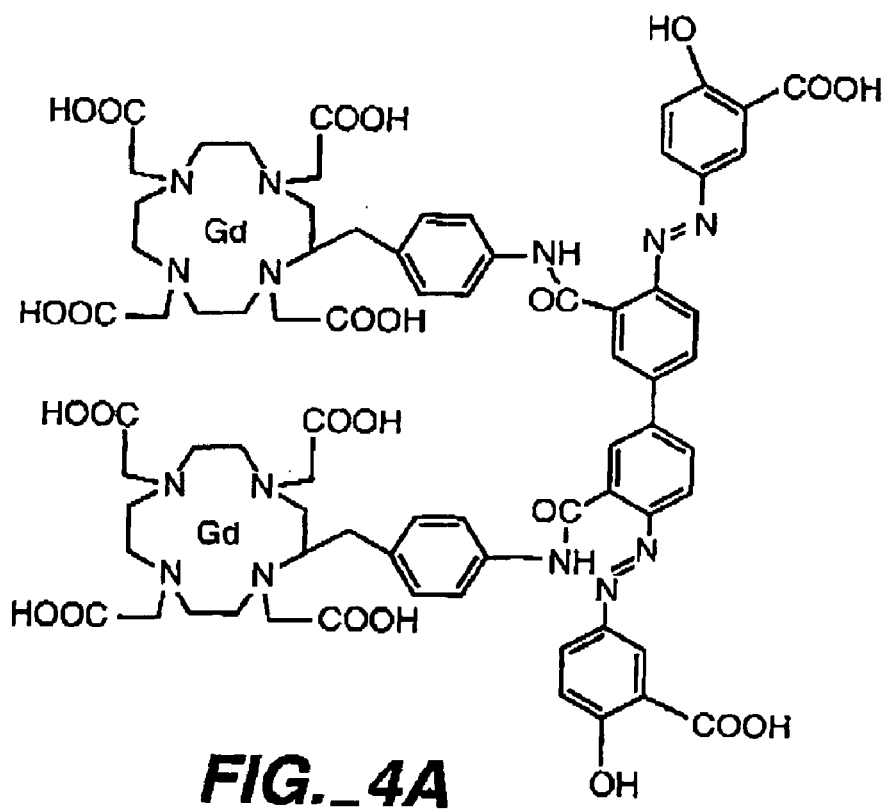
*FIG._4A*
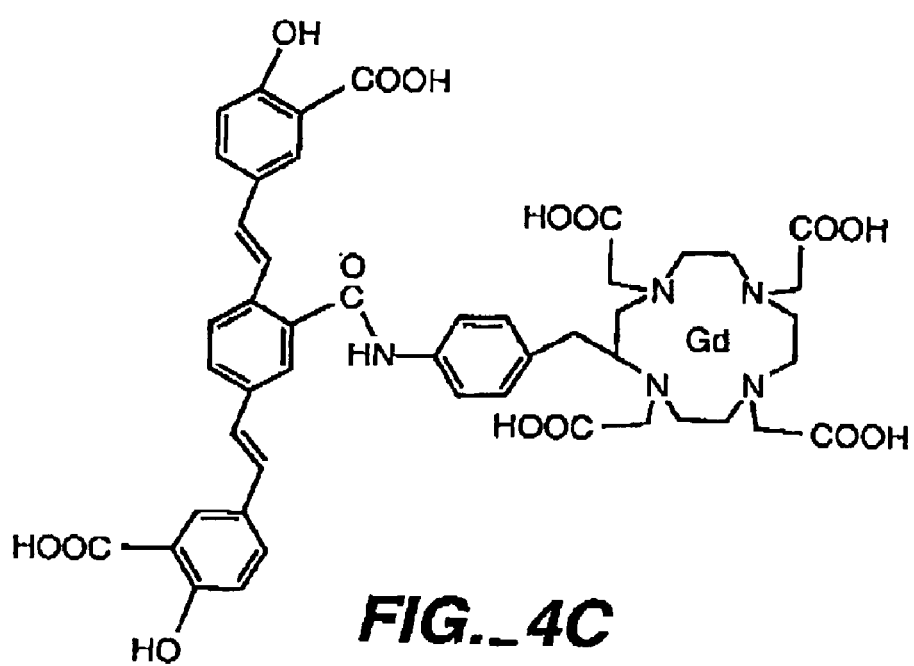
*FIG._4C*

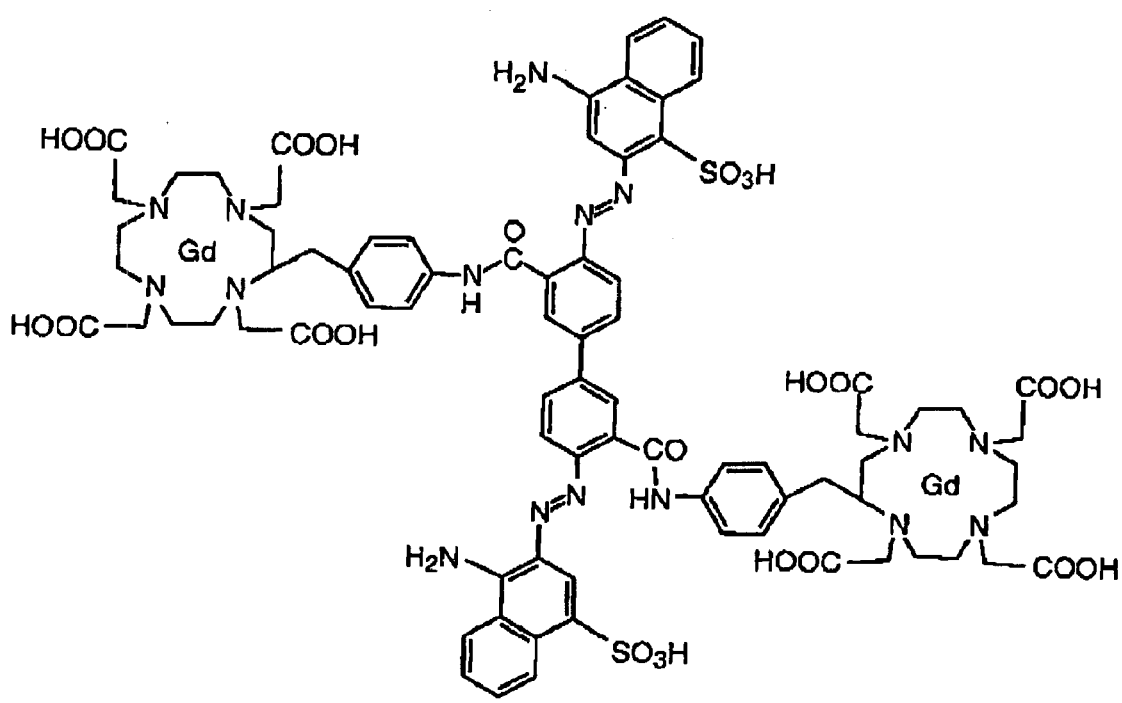
FIG._4B

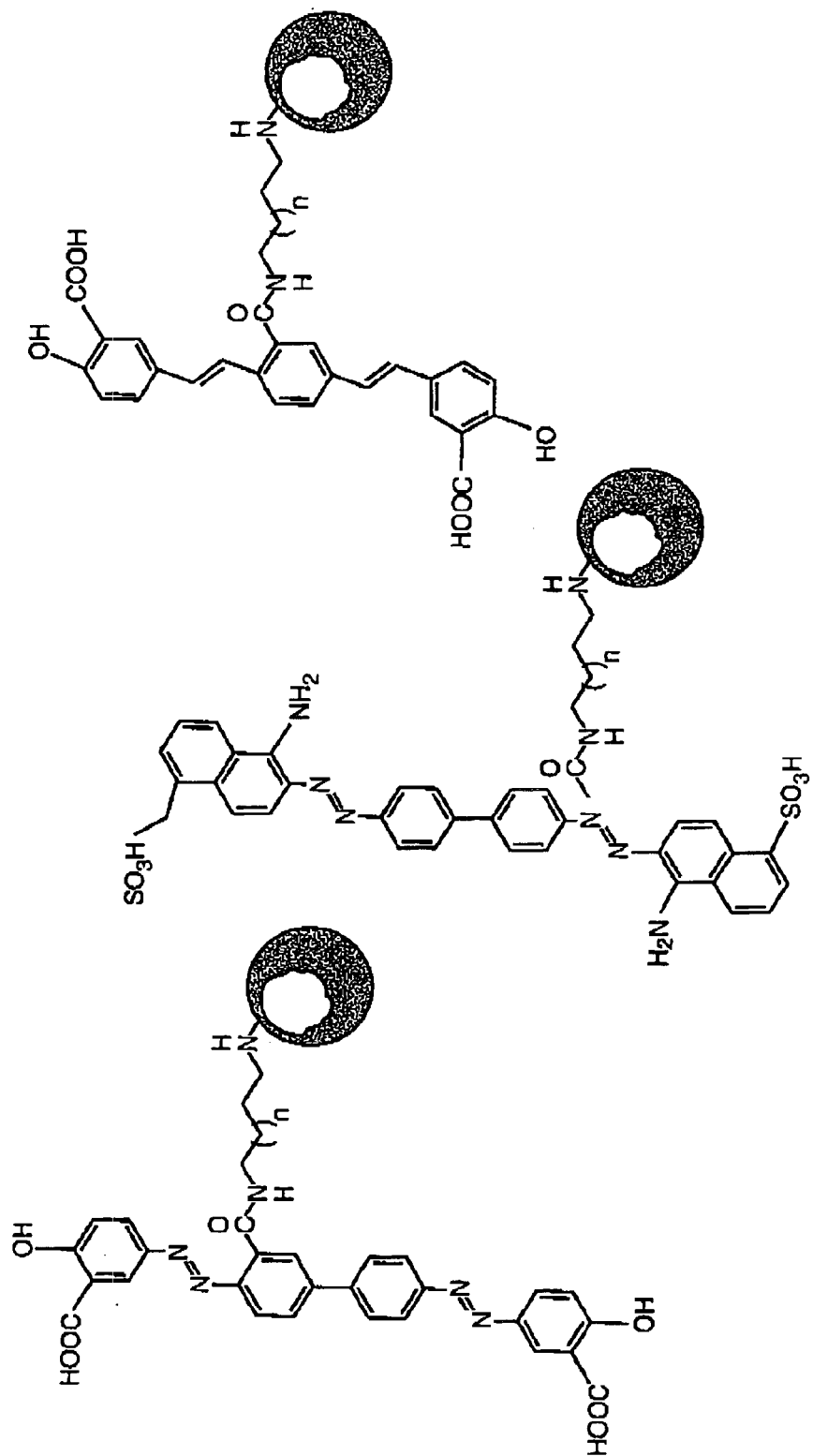
FIG._5

*FIG._6A*
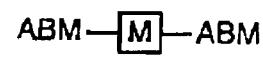
*FIG._6B*
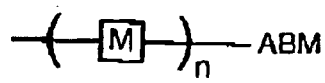
*FIG._6C*
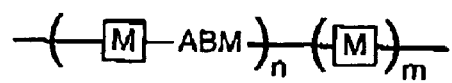
*FIG._6D*
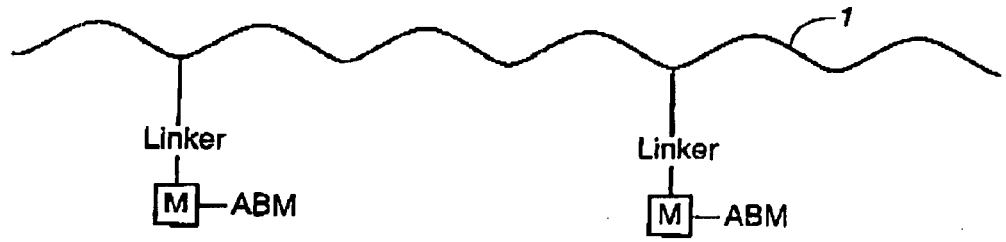
*FIG._6E*
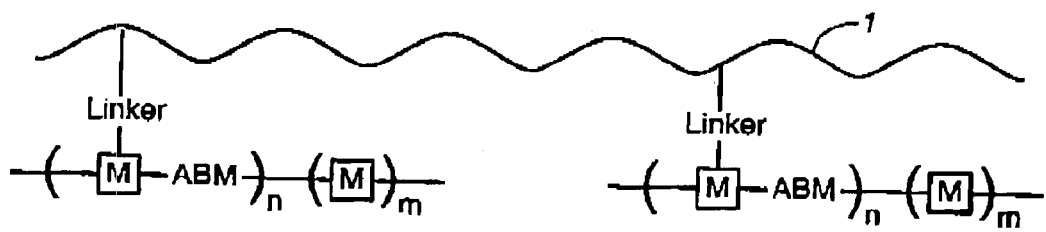
*FIG._6F*

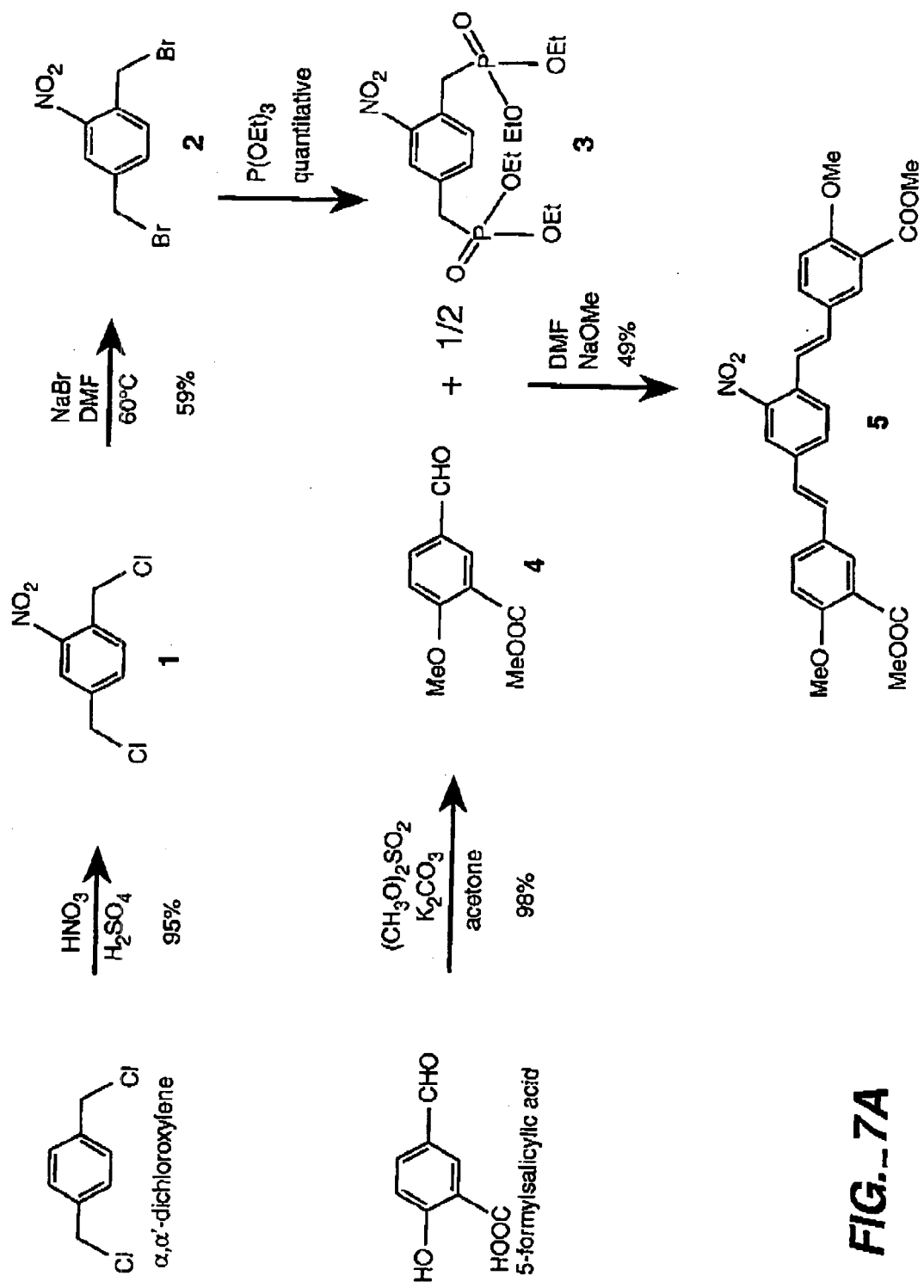
FIG._7A

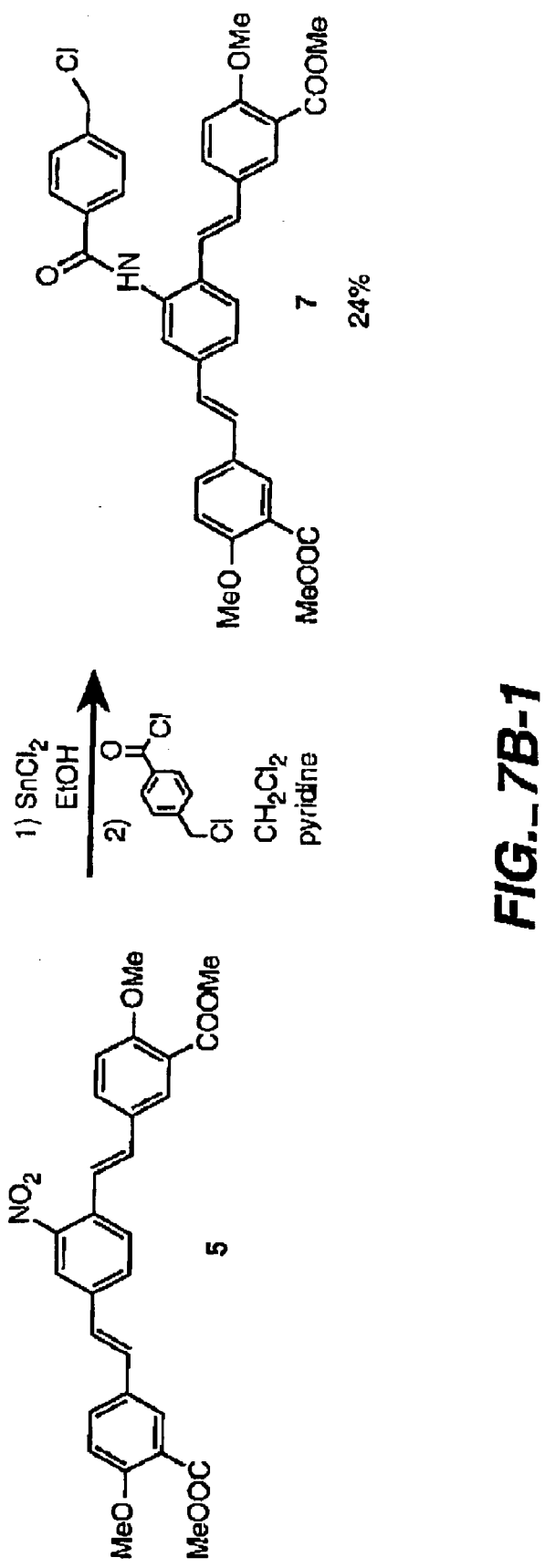
FIG._7B-1

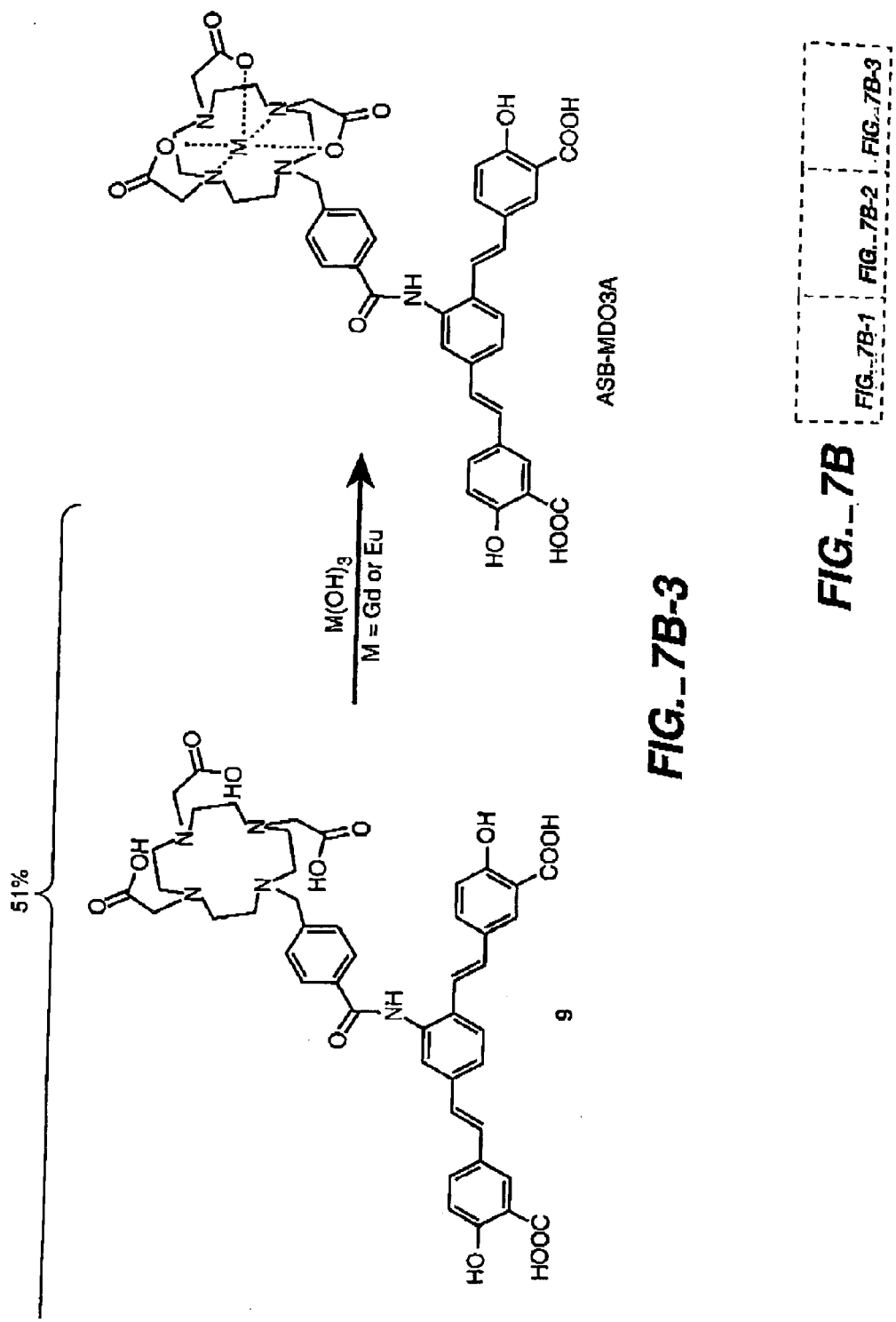

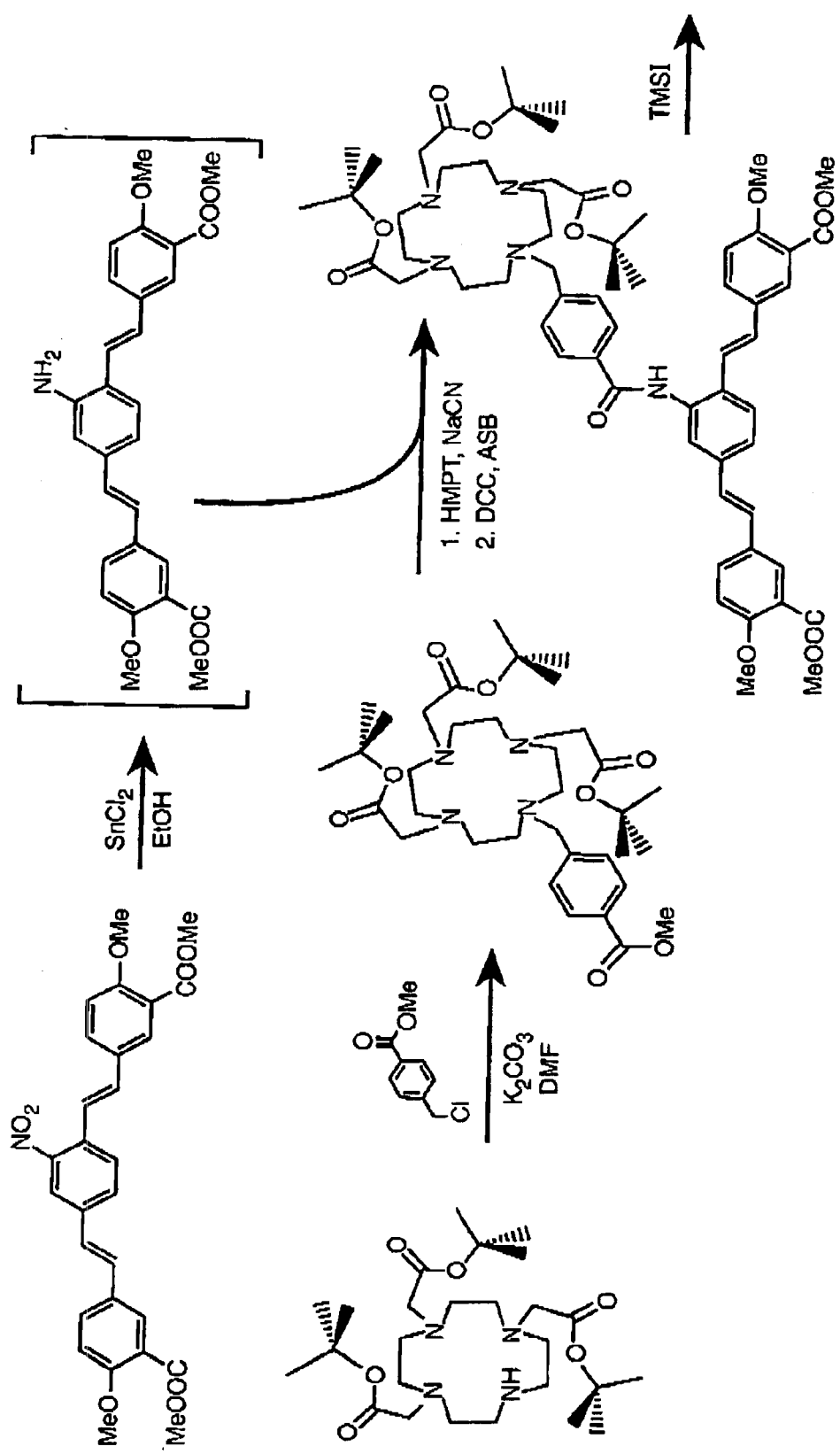
FIG._8A

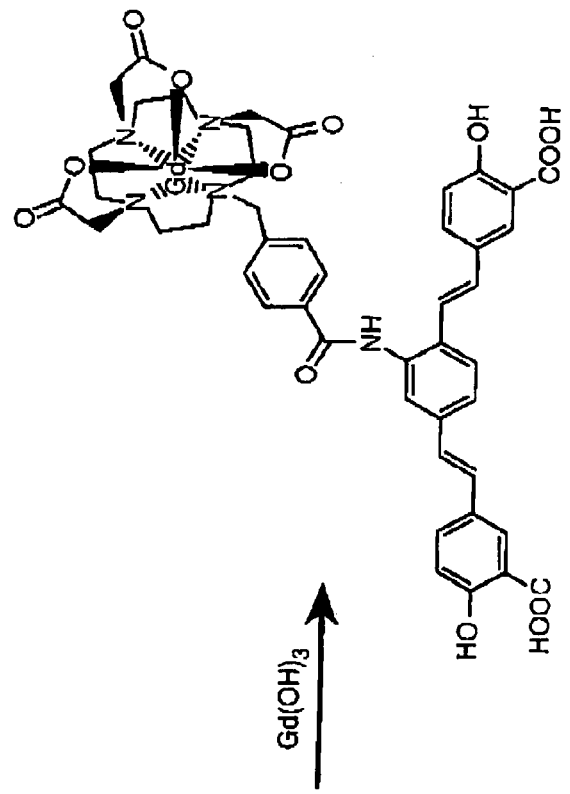
FIG._8B
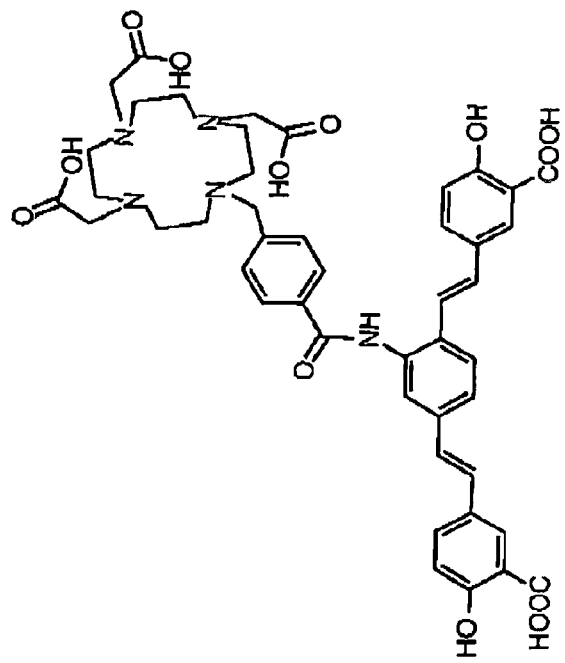
FIG._8
FIG._8A | FIG._8B

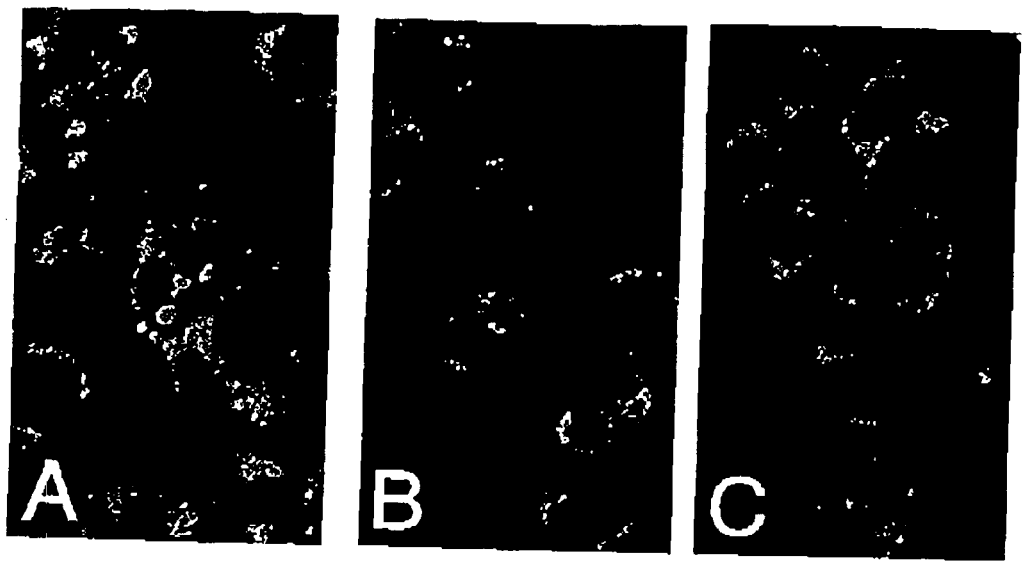
FIG._9A   FIG._9B   FIG._9C

MAGNETIC RESONANCE IMAGING AGENTS FOR IN VIVO LABELING AND DETECTION OF AMYLOID DEPOSITS

This application claims the benefit of the filing date of Ser. No. 60/238,231, filed Oct. 4, 2000 and Ser. No. 60/285,379, filed Apr. 20, 2001.

FIELD OF THE INVENTION

The invention relates to a novel class of magnetic resonance imaging agents that can cross the blood brain barrier and provide accurate magnetic resonance imaging of the brain, especially magnetic resonance images of amyloid deposits associated with Alzheimer's disease.

BACKGROUND OF THE INVENTION

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

The Image

MR images are typically displayed on a gray scale with black the lowest and white the highest measured intensity (I). This measured intensity $I=C*M$, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ & $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans.

The measured intensities in the final image will accurately reflect the spin density (i.e. water content).

Regions with long $T_1$ values compared to the time between scans will progressively lose signal until a steady state condition is reached and will appear as darker regions in the final image. Changes in $T_2$ (spin-spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

MRI Contrast Agents

There is a rapidly growing body of literature demonstrating the clinical effectiveness of paramagnetic contrast agents (currently 8 are in clinical trials or in use). The capacity to differentiate regions/tissues that may be magnetically similar but histologically distinct is a major impetus for the preparation of these agents [1, 2]. In the design of MRI agents, strict attention must be given to a variety of properties that will ultimately effect the physiological outcome apart from the ability to provide contrast enhancement [3]. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is the selection of the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r^6$ dependence) spins. Some paramagnetic ions decrease the $T_1$ without causing substantial linebroadening (e.g. gadolinium (III), ($Gd^{3+}$)), while others induce drastic linebroadening (e.g. superparamagnetic iron oxide). The mechanism of $T_1$ relaxation is generally a through space dipole-dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans in the experiment is short (i.e. $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image). The lanthanide atom $Gd^{3+}$ is by the far the most frequently chosen metal atom for MRI contrast agents because it has a very high magnetic moment ($u^2=63BM^2$), and a symmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (see DTPA below). Several factors influence the stability of chelate complexes include enthalpy and entropy effects (e.g. number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for Gd(DTPA)$^{2-}$ is very high (logK=22.4) and is more commonly known as the formation constant (the higher the logK, the more stable the complex). This thermodynamic parameter indicates the fraction of Gd$^{3+}$ ions that are in the unbound state will be quite small and should not be confused with the rate (kinetic stability) at which the loss of metal occurs ($k_f/k_d$). The water soluble Gd(DTPA)$^{2-}$ chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes.

To date, a number of chelators have been used, including diethylenetriaminepentaacetic (DTPA), 1,4,7,10-tetraazacyclododecane3-N,N'N",N'"-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25: S53 (1990).

Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25: S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7,10-tetraazacyclododecane-N,N',N"N'"-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. Recently, the GdDOTA complex was approved as an MRI contrast agent for use in adults and infants in France and has been administered to over 4500 patients.

Previous work has focused on the development of targeted MRI contrast agents that are relatively inactive, or have weak relaxivity, as contrast enhancement agents in the absence of a physiological target substance, and are activated, thus altering the MR image, in the presence of the physiological target substance. See U.S. Pat. Nos. 5,707,605 and 5,980,862; WO99/21592; and U.S. Ser. Nos. 09/405,046; 60/287,619; 60/203,224 and 60/201,816.

However, it would be desirable to design a class of MRI agents that can cross the blood brain barrier and provide accurate MR imaging of the brain, especially MR images of amyloid deposits associated with Alzheimer's disease.

Alzheimers disease affects over four million American's (Varadarajan, S., et al., (2000) *Journal of Structural Biology*, 130: 184–208). It is defined on the basis of severe memory loss and other cognitive deficits along with the presence of plaques and tangles upon microscopic examination of the brain (*Biological Bases of Brain Function and Disease*, (1994) Fraser, A., Molinoff, P., and Winokur, A. eds., Raven Press, New York). The plaques and tangles are composed of naturally occurring, transmembrane amyloid protein that has become incorrectly folded (Lodish, H., et al., (2000) Molecular Cell Biology, 4th edition, W.H. Freeman and Company, New York).

Definitive diagnosis of Alzheimer's disease requires both a psychological evaluation and a postmortem examination (Khachaturian, Z. S. (1985) *Arch. Neurol.*, 42:1097–1105). Alzheimers disease is difficult to distinguish from normal aging and other ailments such as Pick's disease (Khachaturian, Z. S., (1985) *Arch. Neurol.*, 42:1097–1105) and Huntington's disease (*Biological Bases of Brain Function and Disease*, (1994) Fraser, A., Molinoff, P. and Winokur, A., eds., Raven Press, New York) until very late into the disease. The difficulty of diagnosing Alzheimer's disease is evident upon post-mortem examination when over 20% of the cases are found to have other conditions and not Alzheimer's disease (McKhann, G., et al., (1984), *Neurology*, 34:939–944). Because of poor diagnosis techniques, the study of Alzheimer's disease and search for potential treatments, preventions, or cures remains a daunting task. If a method to locate the plaques responsible for Alzheimer's disease early and accurately existed, the disease would be much easier to diagnose and to study.

Accordingly, it is an object of the present invention to provide MRI contrast or enhancement agents which allow the visualization and detection of amyloid plaques associated with Alzheimer's disease.

SUMMARY OF THE INVENTION

In accordance with the objects outlined above, the present invention provides MRI agent compositions comprising a chelator, comprising a paramagnetic metal ion and an amyloid binding moiety (ABM). The chelator may be directly attached to the ABM or indirectly attached via a linker. The linker may be attached to either an internal or terminal position of the ABM.

In an additional aspect, the invention provides ABMs that are selected from the group consisting of congo red, (trans, trans)-1-bromo-2,5-bis-(3-hydroxycarbonyl4-hydroxy)-styrylbenzene (BSB), and chyrsamine G. These ABMs can be conjugated to chelators such as DOTA, DTPA and DOTEP comprising Gd(III).

In an additional aspect, the invention provides MRI agents comprising chelators linked together using ABMs or polymers.

In a further aspect, the provides pharmaceutical compositions comprising an MRI agent of the invention and a pharmaceutically acceptable carrier.

In an additional aspect, the present invention provides methods of magnetic resonance imaging of a cell, tissue or patient comprising administering an MRI agent of the invention to a cell, tissue or patient and rendering a magnetic resonance image of the cell, tissue or patient.

BRIEF DESCRIPTION OF THE DRAWINGS

FIG. 1 depicts the chemical structures of preferred amyloid binding moieties (ABMs) congo red (FIG. 1A), (trans, trans)-1-bromo-2,5-bis-(3-hydroxycarbonyl-4-hydroxy)-styrylbenzene (BSB; FIG. 1B), and chrysamine G (FIG. 1C).

FIG. 2 depicts sites on ABMs that can be modified and used for the attachment of chelator/paramagnetic metal ion complexes or for the attachment of substitutents. The letter R is used to denote the sites of attachment. FIG. 2A shows sites of attachment for congo red. FIG. 2B shows sites of attachment for BSB. FIG. 2C shows sites of attachment for chyrsamine G.

FIG. 3 depicts a preferred embodiment for attachment of ABMs to a chelator. In this embodiment, the chelator/ paramagnetic metal ion is attached to the terminal phenyl rings of the ABMs. FIGS. 3A and 3B depict the attachment of DOTA-Gd(III) to congo red via a p-aminobenzyl linker. FIG. 3C depicts the attachment of DOTA-Gd(III) to chrysamine G via a p-aminobenzyl linker. FIG. 3D depicts the attachment of DOTA-Gd(III) to BSB via a p-aminobenzyl linker.

FIG. 4 depicts a preferred embodiment for attachment of ABMs to a chelator. In this embodiment, the chelator/paramagnetic metal ion is covalently linked to one of the central phenyl rings. FIG. 4A depicts the attachment of DOTA-Gd(III) to chyrsamine G via a p-aminobenzyl linker. FIG. 4B depicts the attachment of DOTA-Gd(III) to congo red via a p-aminobenzyl linker. FIG. 4C depicts the attachment of DOTA-Gd(III) to BSB via a p-aminobenzyl linker.

FIG. 5 depicts another embodiment. In this embodiment, super paramagnetic iron oxide (SPIO) particles are used. In this embodiment, the SIPOs are coated with carboxyl dextran and attached to the central phenyl rings of the ABMs via carboxyl groups.

FIG. 6 depicts several possible conformation of the dimer embodiments. Boxes represent chelators, with M being the paramagnetic metal ions. FIGS. 6A and 6B represent two possible duplex conformations. In FIGS. 6A and B, the ABM can be directly attached to the chelator/metal ion or indirectly attached via a linker. FIGS. 6C (single MRI agents linked to an ABM) and FIG. 6D (duplex agents) are multimers of MRI contrast agents, wherein n can be from 1 to 1000, with from about 1 to about 20 being preferred, and from about 1 to 10 being especially preferred and m is 0 or 1. FIG. 6E and 6F depicts a polymer (1) as defined herein being attached to either single MRI agents (6E) or multiple MRI agents (6F).

FIGS. 7A through 7B-3 depict a synthetic route for the synthesis of an ABM contrast agent.

FIGS. 8A and 8B depict an improved method of conjugating a modified ABM to GdDOTA to form an MRI contrast agent.

FIG. 9 depicts the results from a cell culture experiment. NIH 3T3 cells were incubated with BSBEuDO3A (see Example 1) for one hour and then examined using fluorescence microscopy. Controls consisted of NIH 3T3 cells (FIG. 9C) and NIH 3T3 cells treated with unconjugated EuDO3A (FIG. 9B). As can be seen from FIG. 9A, in NIH 3T3 cells treated with BSBEuDP3A, a statistically significant amount of BSBEuDO3A was transported across the cell membrane when compared to cells treated with EUDO3A without conjugated BSB (FIG. 9B) and untreated cells (FIG. 9C).

DETAILED DESCRIPTION OF THE INVENTION

Figures 2, 7B:
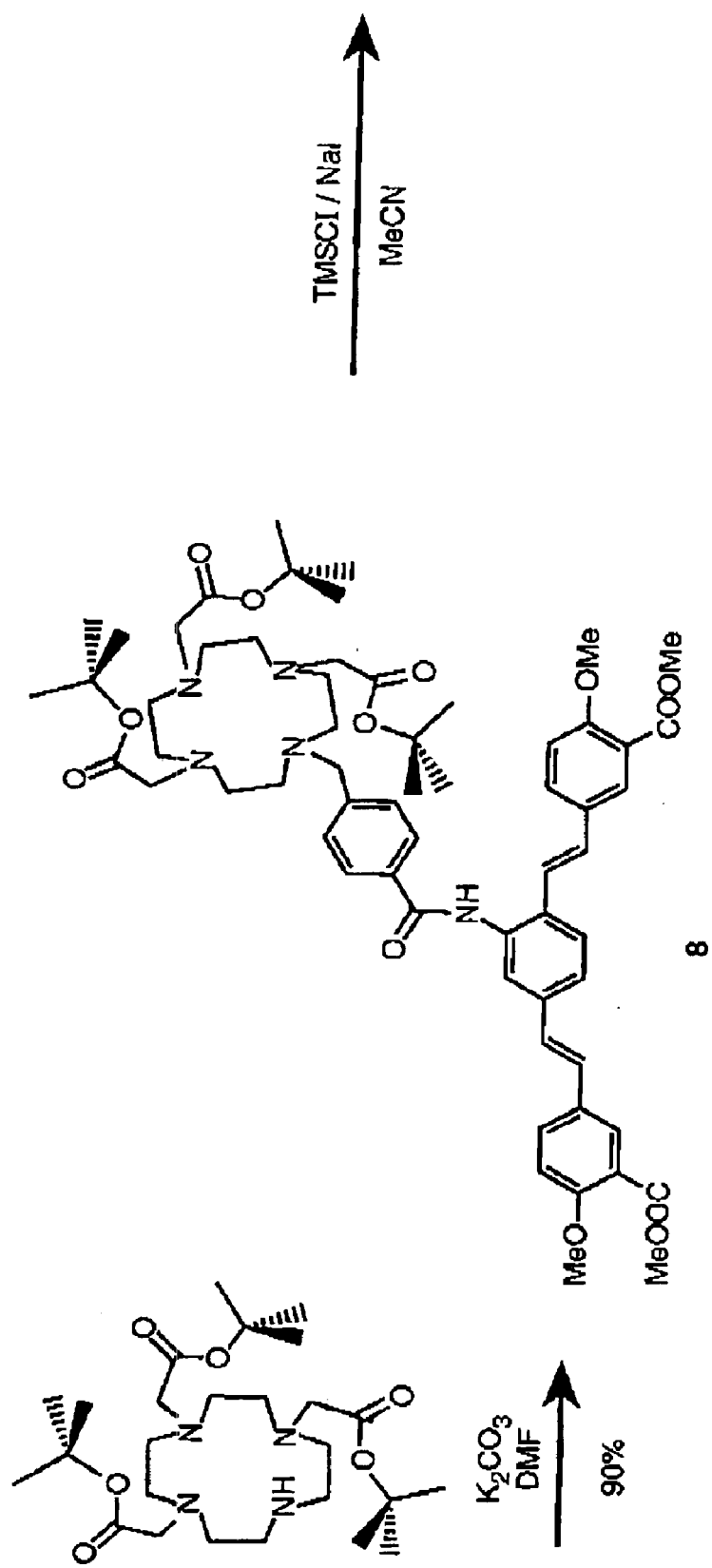

The present invention is directed to a new class of magnetic resonance imaging (MRI) contrast agents and appropriate MR imaging techniques that allow for in vivo visualization of amyloid deposits. Amyloid deposits in the form of plaques and tangles are the defining characteristic of Alzheimer's Disease. The small size and relative lack of contrast between amyloid deposits and the surrounding tissue has made it difficult to visualize these deposits directly with MRI.

The MRI contrast agents of the present invention are designed to be actively transported across the blood brain barrier and label β-amyloid plaques. This is accomplished by chemically linking a contrast agent, such as a gadolinium III based contrast agent, to an amyloid binding moiety (ABM). ABMs are molecules that are capable of crossing the blood brain barrier, permeating cell membranes and specifically labeling β-amyloid plaques (Tweedle, M. F., and Kumar, K., (1999) Top. Biol. Inorg. Chem., 2 (Metallopharmaceuticals II), 1–43; and Emerich, D. F., (2000), Exp. Opin. Ther. Patents, 10:279–287; all of which are hereby incorporated by reference in their entirety).

Accordingly, the MRI contrast agents of the present invention comprise a paramagnetic metal ion bound to a chelator and a amyloid binding moeity (ABM). By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), ytterbium III (Yb+3 or Yb(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator. Due to the relatively high toxicity of many of the paramagnetic ions, the ions are rendered nontoxic in physiological systems by binding to a suitable chelator.

There are a variety of factors which influence the choice and stability of the chelate metal ion complex, including enthalpy and entropy effects (e.g. number, charge and basicity of coordinating groups, ligand field and conformational effects).

In general, the chelator has a number of coordination sites containing coordination atoms which bind the metal ion. The number of coordination sites, and thus the structure of the chelator, depends on the metal ion.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorporated by reference. Thus, as will be understood by those in the art, any of the known paramagnetic metal ion chelators or lanthanide chelators can be easily modified using the teachings herein to further comprise at least one ABM.

A preferred chelator, particularly when the metal ion is Gd(III), is 1,4,7,10-tetraazacyclododecane-N,N',N", N'"-tetracetic acid (DOTA) or substituted DOTA. DOTA has the structure shown below:

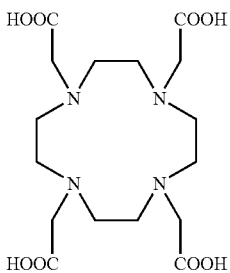

By "substituted DOTA" herein is meant that the DOTA may be substituted at any of the following positions, as shown below:

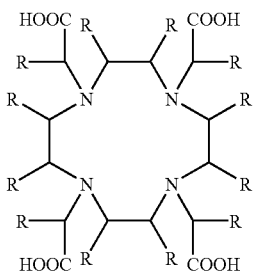

As will be appreciated by those in the art, a wide variety of possible R substituent groups may be used. Suitable R substitution groups, for this and other structures of the invention, include, but are not limited to, hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, and ethers. In addition, suitable substitution groups include substitution groups disclosed for DOTA and DOTA-type compounds in U.S. Pat. Nos. 5,262,532, 4,885,363, and 5,358,704 and WO 98/05625; all of which are expressly incorporated by reference. In some case, the R groups depicted on the chelates may be Abms and the R groups depicted on the ABMs may be the chelators of the invention.

In addition, R groups on adjacent carbons, or adjacent R groups, can be attached to form cycloalkyl or cycloaryl groups, including heterocycloalkyl and heterocycloaryl groups together with the carbon atoms of the chelator, such as is described below and in U.S. Pat. No. 5,358,704, expressly incorporated by reference. These ring structures may be similarly substituted at any position with R groups.

In addition, as will be appreciated by those skilled in the art, each position designated above may have two R groups attached (R' and R"), although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein. In a preferred embodiment, one R group is an ABM and the other R groups are hydrogen; that is, it is preferred to have only two hydrogens at each R position except for the positions occupied by either one or more ABMs or additional chelators, as is outlined below.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary ($-NH_2R$), secondary ($-NHR_2$), or tertiary ($-NR_3$). When the amine is a secondary or tertiary amine, suitable R groups are alkyl groups as defined above.

By "aryl group" or "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc. As for alkyl groups, the aryl group may be substituted with a substitution group, generally depicted herein as R.

By "amino groups" or grammatical equivalents herein is meant $-NH_2$ (amine groups), $-NHR$ and $-NR_2$ groups, with R being as defined herein.

By "nitro group" herein is meant an $-NO_2$ group.

By "sulfur containing moieties" herein is meant compounds containing sulfur atoms, including but not limited to, thia-, thio- and sulfo-compounds (including sulfones ($SO_2$) and sulfides (SO)), thiols ($-SH$ and $-SR$), and sulfides ($-RSR-$).

By "phosphorus containing moieties" herein is meant compounds containing phosphorus, including, but not limited to, phosphines, phosphites and phosphates. A preferred phosphorous moiety is the $-PO(OH)(R)_2$ group. The phosphorus may be an alkyl phosphorus; for example, DOTEP utilizes ethylphosphorus as a substitution group on DOTA. A preferred embodiment has a $-PO(OH)_2R_{25}$ group, with $R_{25}$ being a substitution group as outlined herein.

By "silicon containing moieties" herein is meant compounds containing silicon.

By "ketone" herein is meant an $-RCOR-$ group.

By "aldehyde" herein is meant an $-RCOH$ group.

By "ether" herein is meant an $-R-O-R$ group.

By "alkyoxy group" herein is meant an —OR group.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, alkyl, alkyoxy, amide, hydrogen, aryl and amyloid binding moieties, as is described below.

In an alternative embodiment, a preferred chelator, particularly when the metal ion is Gd(III), is diethylenetriaminepentaacetic acid (DTPA) or substituted DTPA. DPTA has the structure shown below:

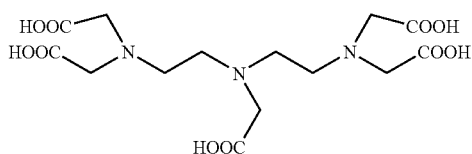

By "substituted DPTA" herein is meant that the DPTA may be substituted at any of the following positions, as shown below:

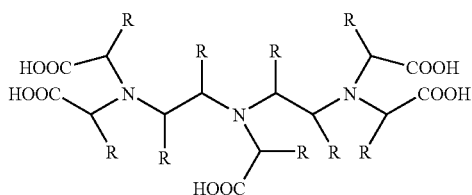

See for example U.S. Pat. No. 5,087,440; which is expressly incorporated herein by reference.

Suitable R substitution groups include those outlined above for DOTA. Again, those skilled in the art will appreciate that there may be two R groups (R' and R") at each position designated above, although as described herein, at least one of the groups at each position is hydrogen, which is generally not depicted herein. In addition, adjacent R groups may be joined to form cycloalkyl or -aryl structures.

In an alternative embodiment, when the metal ion is Gd(III), a preferred chelator is 1,4,7,10-tetraazacyclododecane-N,N',N",N'"-tetraethylphosphorus (DOTEP) or substituted DOTEP (see U.S. Pat. No. 5,188,816). DOTEP has the structure shown below:

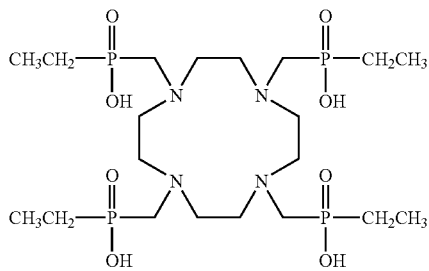

DOTEP may have similar R substitution groups as outlined above.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25: S53 (1990), among others; all of which are expressly incorporated herein by reference.

When the paramagnetic ion is Fe(III), appropriate chelators will have less than 6 coordination atoms, since Fe(III) is capable of binding 6 coordination atoms. Suitable chelators for Fe(III) ions are well known in the art, see for example Lauffer et al., J. Am. Chem. Soc. 109:1622 (1987); Lauffer, Chem. Rev. 87:901–927 (1987); Carvavan, Chem. Rev. 99:2293–2352 (1999); Carvavan, Coord. Chem. Rev. 184:1–157 (1999); and U.S. Pat. Nos. 4,885,363, 5,358,704, and 5,262,532, all which describe chelators suitable for Fe(III); all of which are expressly incorporated herein by reference.

When the paramagnetic ion is Mn(II) (Mn+2), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987); Carvavan, Chem. Rev. 99:2293–2352 (1999); Carvavan, Coord. Chem. Rev. 184:1–157 (1999); and U.S. Pat. Nos. 4,885,363, 5,358,704, and 5,262,532; all of which are expressly incorporated herein by reference.

When the paramagnetic ion is Yb(III), appropriate chelators will have less than 7 or 8 coordination atoms, since Yb(III) is capable of binding 8 or 9 coordination atoms. Suitable chelators for Yb(III) ions include, but are not limited to, DOTA and DPTA and derivatives thereof (see Moi et al., J. Am. Chem.

Soc. 110:6266–6267 (1988)) and those chelators described in U.S. Pat. No. 4,885,363 and others, as outlined above; all of which are expressly incorporated herein by reference.

When the paramagnetic ion is Dy+3 (Dy(III)), appropriate chelators will have less than 7 or 8 coordination atoms, since Dylli is capable of binding 8 or 9 coordination atoms. Suitable chelators are known in the art, as above.

In a preferred embodiment, as is further described below, the chelator and the amyloid binding moiety are covalently linked either directly or through the use of a linker; that is, in the case of direct linkage, the amyloid binding moiety is a substitution group on the chelator. In this embodiment, the substituted chelator, with the bound metal ion, comprises the metal ion complex.

In an alternative embodiment, the chelator and the amyloid binding moiety are indirectly attached. In this embodiment, the chelator and the amyloid binding moiety are attached via a linker, as is further described below.

In one embodiment, chelators are not used. Instead, super paramagnetic iron oxide (SPIO) particles (classical T2 agents) are used. SPIO particles, coated with a variety of polymeric functionalized material, including carboxyl dextran, are commercially available (Miltenyi Biotec Inc.). The particles range in size from approximately 20 nanometers to 5 microns in diameter. Preferably, SPIO particles are attached to the internal phenyl rings of the amyloid binding moiety via the carboxyl groups on the particle's surface (see FIG. 5), although other sites of attachment are possible as further described below. In addition, as each SPIO particle has a number of carboxyl or other functional groups (including amines, sulfonimides, succinimidyl esters, etc.), several amyloid binding moieties can be attached per particle. Using methods well known to those of skill in the art, SPIO particles can be easily modified to further comprise at least one amyloid binding moiety. In addition, SPIO particles with biotin or avidin may be used to attach proteins as well as ABMs to the surface.

By "amyloid binding moiety" or "ABM" herein is meant a molecule that can be actively transported across cell membranes and the blood brain barrier. Preferably, an ABM must be able to label β-amyloid plaques specifically and sensitively, distribute throughout the brain upon intracerebral injection, and maintain its integrity in vivo (Skovronsky, D. M., et al., (2000) *Proc. Natl. Acad. Sci. U.S.A.*, 97:7609–7614; both of which are expressly incorporated herein by reference).

Molecules that bind specifically to amyloid deposits are long conjugated systems possessing multiple phenyl rings with negatively charged groups at each end. It has been suggested that these molecules bind between β-sheets and that lysines on opposing sheets complex with the negatively charged groups on these molecules. Molecules known to bind specifically to amyloid plaques include congo red, (trans, trans)-1-brom-2,5-bis-(3-hydroxycarbonyl4-hydroxy)-styrylbenzene (BSB) and chyrsamine G (Dezutter, et al., (1999) *European Journal of Nuclear Medicine*, 26:1392–1399; Skovronsky, D. M., et al., (2000) *Proc. Natl. Acad. Sci. U.S.A.*, 97:7609–7614). A non-brominated analog of BSB has been used to observe Alzheimer's plaques by fluorescence during autopsies (Klunk, W. E., et al., WO 99/24394; all of which are expressly incorporated herein by reference).

Thus, suitable ABMs for use in the present invention include, but are not limited to, congo red, BSB, and chrysamine G. The chemical structures of congo red, BSB and chyrsamine G are depicted in FIGS. 1A, 1B and 1C, respectively.

The ABM may comprise several components. Preferably, the ABM has a functional moiety which can be used to attach the ABM to a chelator/paramagnetic complex as is described above. For example, replacing the carboxylic or sulfonic acids of the amyloid binding moieties of the present invention will result in efficient MRI contrast agents while preserving the location of the negative charges thought to facilitate amyloid binding. Alternatively, if replacement of the carboxylic acid groups perturbs the amyloid binding properties of the ABM significantly, the chelator/paramagnetic complexes can be covalently linked to one of the central phenyl rings. This latter method of attachment has been shown to not effect the amyloid binding properties of chrysamine G modified with a technectium binding moiety on one of the central phenyl rings.

In addition, the MRI agents of the present invention can be further modified to improve transport across the blood brain barrier, thereby increasing the concentration of the agents in the brain. For example, using techniques well known to those of skill in the art (Fenart, L., et al., (1999) *Journal of Pharmacology and Experimental Terapeutics*, 291:1017–1022; Granholm, A. C., et al., (1998), *Reviews in the Neurosciences*, 9:31–55; Li, X. B., et al., (2000) *Journal of Natural Toxins*, 9:73–83; Rapoport, S. I. (2000) *Celluar and Molecular Neurobiology*, 20:217–230; and, Yoshikawa, T., et al., (1999) *Advanced Drug Delivery Review*, 36:255–275; all of which are expressly incorporated herein by reference). For example, these modifications can include the addition of specific peptides, the use of transferring particles, such as lipid coated charged large particles, SPIO particles coated with charged lipids, etc.

In a preferred embodiment, the ABM is Congo Red. As shown in FIG. 2A, Congo Red can be modified to contain a functional moiety for the attachment of a chelator/paragmagnetic metal ion complex at any site where an R group can be attached. In addition, other components, such as a wide variety of R substituent groups as described above, may be attached at these sites.

In a preferred embodiment, the ABM is BSB. As shown in FIG. 2B, BSB can be modified to contain a functional moiety for the attachment of a chelator/paragmagnetic metal ion complex at any site where an R group can be attached. In addition, other components, such as a wide variety of R substituent groups as described above, may be attached at these sites.

In a preferred embodiment, the ABM is Chyrasmine G. As shown in FIG. 2C, chyrsamine G can be modified to contain a functional moiety for the attachment of a chelator/paragmagnetic metal ion complex at any site where an R group can be attached. In addition, other components, such as a wide variety of R substituent groups as described above, may be attached at these sites.

In other embodiments, ABMs conjugated to chelator/paramagnetic metal ions are used for obtain MR images the brain in the absence of Alzheimer's.

The amyloid binding moieties of the present invention may further comprise a linker group (see FIGS. 3, 4, and 6). Linker groups will be used to optimize the steric considerations of the metal ion complex. In general, the linker group is chosen to allow a degree of structural flexibility.

Generally, suitable linker groups include all R groups listed above (with the exception of hydrogen). Preferred groups include, but are not limited to, alkyl and aryl groups, including substituted alkyl and aryl groups and heteroalkyl (particularly oxo groups) and heteroaryl groups, including alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, ethyl, propyl, butyl, pentyl, hexyl, acetic acid, propionic acid, aminobutyl, p-alkyl phenols, 4-alkylimidazole, carbonyls, OH, COOH, glycols, etc.

The amyloid binding moiety is attached to the metal ion complex in a variety of ways. In a preferred embodiment, as noted above, the amyloid binding moiety is attached to the metal ion complex via a linker group. Alternatively, the amyloid binding moiety is attached directly to the metal ion complex; for example, as outlined below, the amyloid binding moiety may be a substituent group on the chelator.

In a preferred embodiment, at least one of the R groups attached to the internal phenyl rings of the ABMs is used to attach the chelator/paramagnetic metal ion complex. For example, as shown in FIG. 4, a linker can be used to covalently attach a chelator/paramagnetic metal ion complex to one of the internal phenyl rings of an ABM.

In a preferred embodiment, at least one of the R groups attached to the terminal phenyl rings of the ABMs is used to attach the chelator/paramagnetic metal ion complex. For example, as shown in FIG. 3, a linker can be used to covalently attach a chelator/paramagnetic metal ion complex to one of the terminal phenyl rings of an ABM.

As will be appreciated by those in the art, the MRI compositions of the invention may take on a wide variety of different conformations. In a preferred embodiment, the MRI contrast agents are "monomers". Alternatively, in a preferred embodiment, the MRI contrast agents of the invention comprise more than one metal ion, such that the signal is increased. As outlined below, this may be done in a number of ways. FIG. 6 generally depicts a variety of different configurations of the present invention.

In a preferred embodiment, the MRI agents of the invention comprise at least two paramagnetic metals ions, each with a chelator and an ABM; that is multimeric MRI agents are made (see FIG. 6).

In a preferred embodiment, the chelators are linked together, either directly or through the use of a linker or a polymer. For example, using substitution groups that serve as functional groups for chemical attachment on the chelator, attachment to other chelators may be accomplished. As will be appreciated by those in the art, attachment of more than one chelator may also be done via the ABMs.

In one embodiment, the chelators are linked together directly, using at least one functional group on each chelator. In this embodiment, the chelators of the invention include one or more substitution groups that serve as functional groups for chemical attachment. Suitable functional groups include, but are not limited to, amines (preferably primary amines), carboxy groups, and thiols (including SPDP, alkyl and aryl halides, maleimides, α-haloacetyls, and pyridyl disulfides) are useful as functional groups that can allow attachment.

This may be accomplished using any number of stable bifunctional groups well known in the art, including homobifunctional and heterobifunctional linkers (see Pierce Catalog and Handbook, 1994, pages T155–T200, hereby expressly incorporated by reference). This may result in direct linkage, for example when one chelator comprises a primary amine as a functional group and the second comprises a carboxy group as the functional group, and carbodiimide is used as an agent to activate the carboxy for attach by the nucleophilic amine (see Torchilin et al., *Critical Rev. Therapeutic Drug Carrier Systems*, 7(4):275–308 (1991). Alternatively, as will be appreciated by those in the art, the use of some bifunctional linkers results in a short coupling moiety being present in the structure. A "coupling moiety" is capable of covalently linking two or more entities. In this embodiment, one end or part of the coupling moiety is attached to the first MRI contrast agent, and the other is attached to the second MRI agent. The functional group(s) of the coupling moiety are generally attached to additional atoms, such as alkyl or aryl groups (including hetero alkyl and aryl, and substituted derivatives), to form the coupling moiety. Oxo linkers are also preferred. As will be appreciated by those in the art, a wide range of coupling moieties are possible, and are generally only limited by the ability to synthesize the molecule and the reactivity of the functional group. Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated by those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents may be used, similar to the polymer embodiment described below. For example, branched alkyl groups containing multiple functional groups may be desirable in some embodiments.

In an additional embodiment, the linker is a polymer. In this embodiment, a polymer comprising at least one MRI contrast agent of the invention is used. As will be appreciated by those in the art, these MRI contrast agents may be monomeric (i.e. one metal ion, one chelator, one ABM) or a duplex or dimer, as is generally described below (i.e. two metal ions, two chelators, one or more ABMs). The ABMs can be added to the individual monomers, individual dimers (or multimers), or to the polymer. Preferred embodiments utilize a plurality of MRI agents per polymer. The number of MRI agents per polymer will depend on the density of MRI agents per unit length and the length of the polymer.

The character of the polymer will vary, but what is important is that the polymer either contain or can be modified to contain functional groups for the attachment of the MRI contrast agents of the invention. Suitable polymers include, but are not limited to, functionalized dextrans, styrene polymers, polyethylene and derivatives, polyanions including, but not limited to, polymers of heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers; and polycations, including but not limited to, synthetic polycations based on acrylamide and 2-acrylamido-2-methylpropanetrimethylamine, poly(N-ethyl4-vinylpyridine) or similar quarternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, spermine, spermidine and polypeptides such as protamine, the histone polypeptides, polylysine, polyarginine and polyornithine; and mixtures and derivatives of these. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject. As will be appreciated by those in the art, linear and branched polymers may be used. A preferred polymer comprising a polyalkylene oxide is also described in U.S. Pat. No. 5,817,292, incorporated by reference.

A preferred polymer is polylysine, as the —NH$_2$ groups of the lysine side chains at high pH serve as strong nucleophiles for multiple attachment of activated chelating agents. At high pH the lysine monomers are coupled to the MRI agents under conditions that yield on average 5–20% monomer substitution.

In some embodiments, particularly when charged polymers are used, there may be a second polymer of opposite charge to the first that is electrostatically associated with the first polymer, to reduce the overall charge of polymer-MRI agent complex. This second polymer may or may not contain MRI agents. This is particularly useful to cross the blood brain barrier, as neutral complexes can generally be transported.

The size of the polymer may vary substantially. For example, it is known that some nucleic acid vectors can deliver genes up to 100 kilobases in length, and artificial chromosomes (megabases) have been delivered to yeast. Therefore, there is no general size limit to the polymer. However, a preferred size for the polymer is from about 10 to about 50,000 monomer units, with from about 2000 to about 5000 being particularly preferred, and from about 3 to about 25 being especially preferred. In addition, polymers of chelates with a mean molecular weight of between 10–40 kDA serve to distinguish between malignant and benign tumors; see WO 96/35456, hereby incorporated by reference in its entirety.

It should be understood that the multimeric MRI agents of the invention may be made in a variety of ways, including those listed above.

In addition, as will be appreciated by those in the art, when multimeric (all the same monomers) or oligomeric (different monomers)compositions are made, the multimer or oligomer may have one or more ABMs. That is, each chelate may comprise a ABM, or a single oligomer, comprising a plurality of chelates, can have a single ABM; alternatively, less than 1 per chelate may be used but more than 1 per oligomer.

In a preferred embodiment, the MRI contrast agents of the invention are "duplexes". In this embodiment, the MRI duplex comprises two chelators, each with a paramagnetic metal ion, and at least one ABM. In this way, a sort of signal amplification occurs, with two metal ions increasing the signal with a single target molecule. While "duplex" implies two chelators, it is intended to refer to complexes comprising a single ABM. As will be appreciated by those in the art, the MRI agents of this embodiment may have a number of different conformations, as is generally shown in FIG. 6.

As outlined above, the MRI duplex moieties may also be combined into higher oligomers, either by direct linkage or via attachment to a polymer.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532; Meyer et al., (1990), supra, Moi et al., (1988), and McMurray et al., Bioconjugate Chem. 3(2):108–117 (1992); all of which are expressly incorporated herein by reference).

For DOTA derivatives, the synthesis depends on whether nitrogen substitution or carbon substitution of the cyclen ring backbone is desired. For nitrogen substitution, the synthesis begins with cyclen or cyclen derivatives, as is well known in the art; see for example U.S. Pat. Nos. 4,885,363 and 5,358,704; incorporated herein by reference.

For carbon substitution well known techniques are used. See for example Moi et al., supra, and Gansow, supra.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide, in the form of a halide, in the form of a hydroxide, or in the form of a citrate and treated with an equimolar amount of a contrast agent composition. The contrast agent may be added as an aqueous solution or suspension. Dilute acid or base can be added if need to maintain a neutral pH. Heating at temperatures as high as 100° C. may be required.

Synthesis of analogs of ABMs to conjugate to a chelator/metal complex is done using well known techniques. See for example, FIGS. 7–9 and Example 2 which illustrate and describe preferred synthetic routes for the synthesis of MRI contrast agents of the present invention.

The complexes of the invention can be isolated and purified, for example using HPLC systems.

Once isolated and purified, the complexes of the invention can be tested for transport across the blood brain barrier, amyloid binding capability and MRI contrast agent efficiency. For example, standard in vitro relaxivity measurements (i.e., T1 and T2 measurements as a function of concentration of the agent) can be done. Comparisons with the properties of known MRI agents will be used to provide a measure of the efficacy of the ABM MRI as contrast agents.

The complexes of the present invention can be tested in vivo to determine the efficiency of transport across the blood brain barrier using techniques well known in the art. For example, the complexes can be injected into the tail veins of mice to determine how efficiently the complexes traverse the blood brain barrier. MR imaging, fluorescence techniques and immunostaining can be used to visualize the complexes of the invention following injection.

Amyloid binding properties of the complexes to deposits in brain slices can be quantified using standard fluorescence techniques (Skovronshky, D. M., et al., (2000), *Proc. Natl. Acad. Sci. U.S.A.*, 97:7609–7614). The complexes of the present invention can also be steriotaxically injected into brains of transgenic mice known to have significant amyloid deposition (e.g. Tg2576). MR imaging, fluorescence techniques and immunostaining can be used to visualize the complexes of the invention following injection.

Pharmaceutical compositions comprising pharmaceutically acceptable salts of the contrast agents can also be prepared by using a base to neutralize the complexes while they are still in solution. Some of the complexes are formally uncharged and do not need counterions.

Once made, the compositions of the invention find use in a variety of applications. In particular, the metal ion complexes of the invention have use as magnetic resonance imaging contrast or enhancement agents for use in the diagnosis, imaging or monitoring of amyloid plaque formation and Alzeheimer's disease in particular.

The metal ion complexes of the invention may be used in a similar manner to the known gadolinium MRI agents. See for example, Meyer et al., supra; U.S. Pat. No. 5,155,215; U.S. Pat. No. 5,087,440; Margerstadt et al., Magn. Reson. Med. 3:808 (1986); Runge et al., Radiology 166:835 (1988); and Bousquet et al., Radiology 166:693 (1988); all of which are expressly incorporated herein by reference. The metal ion complexes are administered to a cell, tissue or patient as is known in the art. A "patient" for the purposes of the present invention includes both humans and other-animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

The administration of the agents of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the staining of histological samples, etc., the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise an MRI agent in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In addition, in one embodiment, the MRI agents are added in a micellular formulation; see U.S. Pat. No. 5,833,948, hereby incorporated by reference.

Combinations of the compositions may be administered. Moreover, the compositions may be administered in combination with other therapeutics or imaging agents.

Generally, sterile aqueous solutions of the contrast agent complexes of the invention are administered to a patient in a variety of ways, including orally, intrathecally and especially intraveneously in concentrations of 0.003 to 1.0 molar, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704; both of which are incorporated herein by reference.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers, including polyethylene glycol, to the chelator (see U.S. Pat. Nos. 5,155,215 and 5,605,672). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference, including U.S. Pat. Nos. 5,707,605 and 5,980,862; WO99/21592; and U.S. Ser. Nos. 09/405,046; 60/287,619; 60/203,224 and 60/201,816, 60/238,231 and 60/285,379.

EXAMPLES

Example 1

Synthesis and Testing of an MRI Contrast Agent

A synthetic method for synthesizing conjugating an analog of BSB to a contrast agent was designed. A synthetic route was engineered to make the MRI contrast agent BSBGdDO3A. The synthesis is ten steps long and links BSB to DO3A, a common contrast agent. The steps involved in the synthesis of BSBDo3A are shown in FIG. 7.

Once the compound was synthesized, a cell culture experiment was performed. In this experiment, europium was used instead gadolinium because europium has a higher fluorescence lifetime than gadolinium, thus making it easier to visualize by fluorescence microscopy.

NIH 3T3 cells were incubated with BSBEuDO3A for one hour then rinsed and examined using fluorescence microscopy with a two-photon microscope. The control experiments consisted of untreated cells as well as cells incubated with unconjugated EuDO3A.

The results, showed that a statistically significant amount of BSBEuDO3A was transported across the cell membrane of NIH 3T3 cells, when compared to cells treated with EuDO3A without conjugated BSB and untreated cells (see FIG. 10). In addition, transport of BSBEuDO3A across the cell membrane without killing the cells.

Example 2

Experimental Method for Synthesizing a Modified ABM

Starting Materials and Methods of Analysis

All reagents and solvents were the purest commercially available and used without further purification. (S)4-Nitrophenylalanine was purchased from Advanced Chemtech. Hydrogen chloride was purchased from Matheson. Anhydrous solvents and all other starting materials were purchased from Aldrich. Methyl (S)-p-nitrophenylalanate (3)[49] and N-((methoxycarbonyl)methyl)-4-nitrophenylaline methyl ester (10)[48] were prepared by literature routes. (Note: In the synthesis of 10 if anhydrous DMF is used as the solvent for the free-basing, a sludge forms, making reaction with methyl bromoacetate extremely difficult. If, instead, non-anhydrous DMF is used for the free-basing, then removed, and anhydrous DMF is used for the substitution, the reaction runs smoothly.)

$^1$H, $^{13}$C, and $^{31}$P NMR spectra were obtained on a Varian mercury spectrometer at 300, 75.5, and 123 MHz, respectively. For samples in CDCl$_3$, values of 7.27 and 77.23 ppm were used as internal reference for the $^1$H and $^{13}$C spectra, respectively. $^{31}$P spectra were externally referenced with 85% H$_3$PO$_4$ having a value of 0.00 ppm. Mass spectrometry samples were analyzed using electrospray (ESI) ionization, quadrupole mass spectrometry in the PPMAL Protein/Peptide MicroAnalytical Laboratory, California Institute of Technology, Beckman Institute. Results reported for m/z are for [M+H$^+$]$^+$. FTIR samples were prepared as nujol mulls. A Perkin Elmer 1600 series FTIR spectrophotometer was used in collecting and analyzing spectra. Thin-layer chromatography (TLC) was run on aluminum-backed silica gel plates with 0.2-mm-thick silica gel 60 F 254 (Merck, Germany) and observed with a 254 nm lamp. Elemental analyses were performed at Desert Analytics Laboratory, Tucson, Ariz.

Synthesis of Compounds 1,4-bis(chloromethyl)-2-nitrobenzene (4):

To 15.0 g (0.0857 mol) of α,α'-dichloro-p-xylene was added 10 mL of 60% nitric acid at 0° C. followed by 15 mL of 95% sulfuric acid. The mixture was stirred and heated at 60° C. for 2 hours. The yellow reaction mixture was then poured onto 500 mL of ice/water. An oil layer formed below the ice/water and quickly solidified. Dichloromethane was added to dissolve the solid. The dichloromethane layer was separated and dried over MgSO$_4$. Solvent was removed under reduced pressure, and the solid was dried in vacuo to give 17.9 g (95%) of a yellow powder. $^1$H NMR (CDCl$_3$): δ=4.64 (s, 2H), 4.97 (s, 2H), 7.70 (s, 2H), 8.10 (s, 1H); $^{13}$C NMR (CDCl$_3$): δ=44.67, 44.28, 125.14, 132.11, 132.31, 133.53, 139.45, 147.84; IR (nujol): 1537 and 1352 cm$^{-1}$ n(N=O); TLC: R$_f$=0.78 (ethyl acetate/hexanes, 1:1); Anal. Calcd for C$_8$H$_7$C$_{12}$NO$_2$: C, 43.67; H, 3.21; N, 6.37. Found: C, 43.68; H, 3.20; N, 6.32 (see FIG. 8A).

1,4-bis(bromomethyl)-2-nitrobenzene (5):

To 29.50 g (0.1338 mol) of 4 in 150 mL DMF was added 206.5 g (2.00 mol) of sodium bromide. The mixture was stirred at 60° C. for 4 hours, after which time the reaction mixture was poured into 800 mL ice/water. Dichloromethane (200 mL) was added, and the organic layer was separated and dried over MgSO$_4$. Solvent was removed under reduced pressure. Crystallization from ethanol afforded 24.2 g (59%) of light orange needles. $^1$H NMR (CDCl$_3$): δ=4.50 (s, 2H), 4.82 (s, 2H), 7.57 (d, J=7.9 Hz, 1H), 7.64 (dd, J=7.9 Hz, 1.9 Hz, 1H), 8.08 (d, J=1.9 Hz, 1H); $^{13}$C NMR (CDCl$_3$): δ=28.71, 30.82, 125.88, 132.71, 133.14, 134.08, 139.96, 147.82; TLC R$_f$=0.57 (ethyl acetate/hexanes, 1:1); Anal. Calcd for C$_8$H$_7$Br$_2$NO$_2$: C, 31.10; H, 2.28; N, 4.53. Found: C, 31.38; H, 2.44; N, 4.55 (see FIG. 8A).

2,5bis(diethylphosphonatomethyl)nitrobenzene (6):

To 7.73 g (0.0250 mol) of 5 was added 8.98 mL (0.0524 mol) of triethylphosphite. The resulting mixture was refluxed until evolution of ethylbromide ceased. The brown solution was cooled to room temperature, and excess triethylphosphite was distilled off under full vacuum at room temperature, leaving behind 10.6 g (quantitative) of extremely viscous orange oil. $^1$H NMR (CDCl$_3$): δ=1.25 (m, 12H), 3.19 (d, J=22 Hz, 2H), 3.68 (d, J=22 Hz, 2H), 4.05 (m, 8H), 7.24 (dd, J=7.9 Hz, 2.4 Hz, 1H), 7.51 (d, J=7.9 Hz, 1H), 7.89 (d, J=2.4 Hz, 1H); $^{13}$C NMR (CDCl$_3$): δ=16.38 (m), 29.40 (m), 31.20 (m), 32.18 (m), 34.01 (m), 62.36 (m), 125.71 (m), 126.16 (m), 132.60 (m), 133.18 (m), 134.17 (m), 149.05 (m); $^{31}$P NMR (CDCl$_3$): δ=25.0 (d, J=8.2 Hz), 25.5 (d, J=8.2 Hz); MS Calcd for C$_{16}$H$_{27}$NO$_8$P$_2$[M+H$^+$]$^+$: 424.3, found 424.2; Anal. Calcd for C$_{16}$H$_{27}$NO$_8$P$_2$: C, 45.40; H, 6.43; N, 3.31. Found: C, 45.35; H, 6.55; N, 3.32 (see FIG. 8A).

3-formyl-5-methoxymethylbenzoate (7):

5-formylsalicylic acid (1.00 g, 0.00602 mol), potassium carbonate (4.00 g, 0.0289 mol), and dimethylsulfate (1.29 mL, 0.0137 mol) were refluxed in acetone (50 mL) for 4 hours. The reaction mixture was allowed to cool to room temperature (RT); then 1.70 mL of water was added and stirred for 2 hours. Inorganics were filtered off, and solvent was removed from filtrate under reduced pressure to give a brown residue. The residue was taken up in dichloromethane, washed with water, dried over MgSO$_4$, and solvent was removed under reduced pressure to give 1.14 g (98%) of a light tan solid. $^1$H NMR (CDCl$_3$): δ=3.93 (s, 3H), 4.02 (s, 3H), 7.12 (d, J=8.7 Hz, 1H), 8,04 (dd, J=8.7 Hz, 2.2 Hz, 1H), 8.34 (d, J=2.2 Hz, 1H), 9.93 (s, 1H); $^{13}$C NMR (CDCl$_3$): δ=52.45, 56.61, 112.35, 120.53, 129.05, 134.30,134.54, 163.55, 165.40,189.97; IR (nujol): 1703 cm$_{-1}$n(C=O); TLC: R$_f$=0.26 (ethyl acetate/hexanes, 1:2); MS Calcd for C$_1$OH$_{10}$O$_4$[M+H$^+$]$^+$: 195.2, found 195.2; Anal. Calcd for C$_1$OH$_{10}$O$_4$: C, 61.85; H, 5.19. Found: C, 61.88; H, 5.08 (see FIG. 8A).

(trans,trans)-1-nitro-2,5-bis-(3-methoxycarbonyl-4-methoxy)-stytylbenzene (8):

To a stirred solution of 6 (0.545 9, 0.00129 mol) in 7 mL of DMF was added dropwise sodium methoxide (0.154 g, 0.00286 mol) in 3 mL of DMF. Upon addition the orange solution of 6 turned purple. After stirring for 5 min, 7 (0.500 g, 0.0026 mol) was added and the reaction mixture turned green. After stirring for 30 min under argon, the mixture was poured into 50 mL of ice/water. Liquids were removed under reduced pressure, and the residue was taken up in benzene and filtered over a silica gel plug to remove inorganic products. Silica gel chromatography (ethyl acetate/hexanes, 1:2) yielded 0.320 g (49.4%) of bright orange solid. $^1$H NMR (CDCl$_3$): δ=3.92(m, 12H), 6.94 (d, J=16.4 Hz, 1H), 6.96 (m, 2H), 7.02 (d, J=16.1 Hz, 1H), 7.09 (d, J=16.4 Hz, 1H), 7.43 (d, J=16.1 Hz, 1H), 7.62 (m, 4H), 7.95 (m, 3H);

$^{13}$C NMR (CDCl$_3$): δ=52.38, 56.34, 112.46, 120.30, 120.35, 121.94, 122.24, 124.85, 127.95, 128.69, 128.88, 129.70, 130.08, 130.24, 130.68, 131.15, 131.72, 131.79, 132.01, 137.45, 148.19, 159.13, 159.26, 166.28, 166.32; TLC: R$_f$=0.09 (ethyl acetate/hexanes, 1:2); MS Calcd for C$_{28}$H$_{25}$NO$_8$[M+H$^+$]$^+$: 504.5, found 504.2; Anal. Calcd for C$_{28}$H$_{25}$NO$_8$: C, 66.79; H, 5.00; N, 2.78. Found: C, 66.71; H, 5.05; N, 2.83 (see FIG. 8A).

(trans,trans)-1-nitro-2,5-bis-(3-hydroxycarbonyl-4-methoxy)-styrylbenzene:

To a solution of 8 (0.500 g, 0.993 mmol) in 10 mL of dichloromethane at 70° C. under argon was slowly added a solution of boron tribromide (0.424 mL, 4.49 mmol) in 10 mL of dichloromethane. Upon completion of the addition, the reaction was stirred for 1 hour at 70° C. before being poured onto 10 g of ice containing 0.5 mL of concentrated hydrochloric acid. The organic layer was separated and the aqueous layer was washed with dichloromethane. The combined organic layer were concentrated under reduced pressure and purified by silica gel chromatography (hexanes/ethyl acetate 1:1) to give 0.218 g (46%) of a tan solid. $^1$H NMR (CDCl$_3$): δ=3.99 (m, 6H), 7.01 (m, 5H), 7.28 (d, J=16.2 Hz, 1H), 7.64 (m, 5H), 7.97 (m, 2H), 10.85 (s, 1H), 10.88 (s, 1H); TLC: R$_f$=0.63 (ethyl acetate/hexanes, 1:1); MS Calcd for C$_{26}$H$_{21}$NO$_8$[M+H$^+$]$^+$: 476.5, found 476.0.

(trans,trans)-1-nitro-2,5-bis-(3-hydroxycarbonyl-4-hydroxy)-styrylbenzene:

A solution of 8 (0.5 g, 0.993 mmol) and lithium chloride (0.505 g, 0.0119 mol) in 10 mL of DMF was refluxed for 22 hours under argon. After cooling to room temperature, 30 mL of 10% aqueous sodium hydroxide was added. The solution was washed with 2×25 mL of diethyl ether. The aqueous layer was then acidified with 50 mL of 10% aqueous hydrochloric acid and extracted with diethyl ether. The organic washings from the acidic solution were washed with brine, dried over sodium sulfate, and concentrated under reduced pressure. Silica gel chromatography (ethyl acetate followed by methanol) yielded 0.356 g (80%) of a yellow solid. TLC: R$_f$=0.00 (ethyl acetate), 1.00 (methanol); MS Calcd for C$_{24}$H$_{17}$NO$_8$[M+H$^+$]$^+$: 448.4, found 448.2.

Example 3

In vivo Testing of the MRI Contrast Agents

The MRI contrast agents will be steriotaxically injected into the brains (hippocampus or lateral ventricle) of transgenic mice known to have significant amyloid deposition (e.g., Tg2576). Contra-lateral injection of MRI contrast agents known not to bind to amyloid deposits will provide an internal control After recovery, the mice will be imaged in a 11.7T MR scanner periodically over the course of several days to follow the diffusion of the initial bolus of the injected contrast agent, and subsequent amyloid binding. Spin-echo, gradient echo, and a number of fast MR imaging methods will be tested to see which provides the best combination of contrast and signal in the least amount of time. After MR imaging, the mice will be sacrificed, brains removed, frozen, sliced, examined with fluorescence microscopy to determine the location of the contrast agent, and then immunoassayed for amyloid. Coincidence of location of the contrast agent in the MR and fluorescence images with the immunostain will be conclusive evidence of the efficacy of the methodology.

We claim:
1. An MRI agent comprising:
   a) a chelator;
   b) a lanthanide metal ion; and,
   c) an amyloid binding moiety (ABM) comprising (trans, trans)-1-bromo-2,5-bis-(3-hydroxycarbonyl-4-hydroxy)-styrylbenzene (BSB) or a derivative thereof.
2. An MRI agent according to claim 1 wherein said lanthanide metal ion is gadolinium III (Gd+3 or Gd(III)).
3. An MRI agent according to claim 1 wherein said lanthanide metal ion is dysprosium (Dy+3 or Dy(III)).
4. An MRI agent according to claim 1 wherein said lanthanide metal ion is europium (Eu+3 or Eu(III)).
5. An MRI agent according to claim 1, 2, 3, or 4 wherein said chelator is 1,4,7,10-tetraazacyclododecane-N,N'N",N"'-tetracetic acid (DOTA) or a derivative thereof.
6. An MRI agent according to claim 1, 2, 3 or 4 wherein said chelator is diethylenetriaminepentaacetic acid (DTPA) or a derivative thereof.
7. An MRI agent according to claim 1, 2, 3, or 4 wherein said chelator is 1,4,7,10-tetraazacyclododecane-N,N'N",N"'-tetraethylphosphorus (DOTEP) or a derivative thereof.
8. An MRI agent composition according to claim 1 wherein said chelator is directly attached to said ABM.
9. An MRI agent composition according to claim 1 wherein said chelator is indirectly attached to said ABM via a linker.
10. An MRI agent composition according to claim 9 wherein said linker is attached to an internal position of said ABM.
11. An MRI agent composition according to claim 9 wherein said linker is attached to a terminus of said ABM.
12. An MRI agent composition according to claim 9, 10, or 11 wherein said linker is selected from the group consisting of an aryl or alkyl group.
13. An MRI agent composition according to claim 1 having the formula:

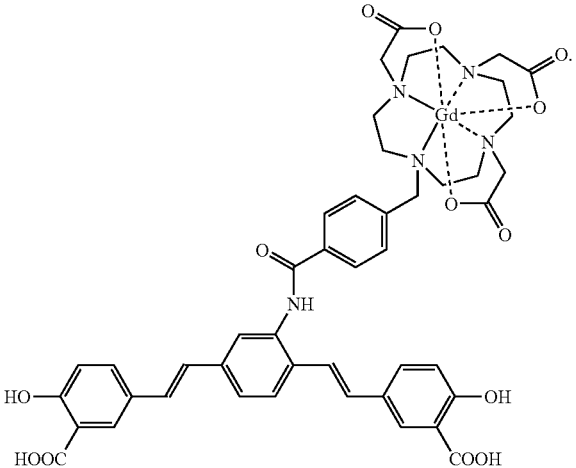

14. A pharmaceutical composition comprising an MRI agent composition as in any one of claims 1, 4, 8–11 and 13, and a pharmaceutically acceptable carrier.
15. A method of magnetic resonance imaging of a cell, tissue or patient comprising administering an MRI agent as in any one of claims 1–4, 8–11 and 13 to a cell, tissue or patient and rendering a magnetic resonance image of said cell, tissue or patient.

* * * * *

UNITED STATES PATENT AND TRADEMARK OFFICE
CERTIFICATE OF CORRECTION

PATENT NO. : 7,029,655 B2 Page 1 of 1
APPLICATION NO. : 09/972302
DATED : April 18, 2006
INVENTOR(S) : Matthew J. Allen, Scott Fraser, Russell E. Jacobs, Thomas J. Meade It is certified that error appears in the above-identified patent and that said Letters Patent is hereby corrected as shown below:

In column 22, line 59, please replace the text from "Claims 1, 4, 8-11 and 13" to -- Claims 1-4, 8-11 and 13 --

Signed and Sealed this

Fifteenth Day of August, 2006

JON W. DUDAS
*Director of the United States Patent and Trademark Office*